US008679499B2

(12) United States Patent
Strober et al.

(10) Patent No.: US 8,679,499 B2
(45) Date of Patent: *Mar. 25, 2014

(54) METHODS FOR RELIEVING ASTHMA-ASSOCIATED AIRWAY HYPERRESPONSIVENESS

(75) Inventors: Samuel Strober, Stanford, CA (US); Everett Hurteau Meyer, Redwood City, CA (US); Dale T. Umetsu, Newton, MA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 300 days.

This patent is subject to a terminal disclaimer.

(21) Appl. No.: 12/697,882

(22) Filed: Feb. 1, 2010

(65) Prior Publication Data
US 2010/0197613 A1 Aug. 5, 2010

Related U.S. Application Data

(63) Continuation of application No. 11/266,033, filed on Nov. 2, 2005, now Pat. No. 7,682,614.

(60) Provisional application No. 60/706,548, filed on Aug. 8, 2005, provisional application No. 60/624,568, filed on Nov. 2, 2004.

(51) Int. Cl.
A61K 39/395 (2006.01)
A61P 37/08 (2006.01)
A61P 11/06 (2006.01)
A61K 31/7032 (2006.01)

(52) U.S. Cl.
USPC .................... 424/144.1; 424/154.1

(58) Field of Classification Search
None
See application file for complete search history.

(56) References Cited

U.S. PATENT DOCUMENTS

| 5,679,347 | A | 10/1997 | Porcelli et al. |
|---|---|---|---|
| 6,197,582 | B1 | 3/2001 | Trakht |
| 6,531,453 | B1 | 3/2003 | Taniguchi et al. |
| 6,555,372 | B1 | 4/2003 | Motoki |
| 6,747,010 | B2 | 6/2004 | Taniguchi et al. |
| 6,800,738 | B1 | 10/2004 | Carter et al. |
| 7,041,870 | B2 | 5/2006 | Tomizuka et al. |
| 7,063,844 | B2 | 6/2006 | Porcelli et al. |
| 7,273,852 | B2 | 9/2007 | Tsuji |
| 7,419,958 | B2 | 9/2008 | Wilson et al. |
| 7,488,491 | B2 | 2/2009 | Tsuji et al. |
| 2001/0051156 | A1 | 12/2001 | Zeng et al. |
| 2002/0071842 | A1 | 6/2002 | Gumperz et al. |
| 2002/0115624 | A1 | 8/2002 | Behar et al. |
| 2002/0164331 | A1 | 11/2002 | Exley et al. |
| 2002/0172677 | A1* | 11/2002 | Lahn et al. .................. 424/145.1 |
| 2003/0064967 | A1 | 4/2003 | Luchoomun et al. |
| 2003/0206914 | A1 | 11/2003 | Porcelli et al. |
| 2004/0009594 | A1 | 1/2004 | Wakasugi |
| 2004/0073957 | A1 | 4/2004 | Tomizuka et al. |
| 2004/0087485 | A1 | 5/2004 | Ilan et al. |
| 2004/0171522 | A1 | 9/2004 | Ilan et al. |
| 2004/0171526 | A1 | 9/2004 | Ilan et al. |
| 2004/0171527 | A1 | 9/2004 | Ilan et al. |
| 2004/0171528 | A1 | 9/2004 | Ilan et al. |
| 2004/0171557 | A1 | 9/2004 | Ilan et al. |
| 2004/0235162 | A1 | 11/2004 | Sato |
| 2005/0032210 | A1 | 2/2005 | Sato et al. |
| 2007/0104776 | A1 | 5/2007 | Ishii et al. |

FOREIGN PATENT DOCUMENTS

| EP | 1767216 A1 | 3/2007 |
|---|---|---|
| WO | 95/00163 A1 | 1/1995 |
| WO | 00/02583 | 1/2000 |
| WO | 00/02923 | 1/2000 |
| WO | 01/94949 A2 | 12/2001 |
| WO | 03/092615 A2 | 11/2003 |
| WO | 03/092615 A3 | 11/2003 |
| WO | 04/001655 A1 | 12/2003 |
| WO | 2004/019900 A1 | 3/2004 |
| WO | 2004/028475 A2 | 4/2004 |
| WO | 2004/084874 A2 | 10/2004 |
| WO | 2004/094444 A1 | 11/2004 |
| WO | 2005/014008 A2 | 2/2005 |
| WO | 2005/014008 A3 | 2/2005 |
| WO | 2005/032462 A2 | 4/2005 |
| WO | 2005/032462 A3 | 4/2005 |
| WO | 2005/120574 A1 | 12/2005 |

OTHER PUBLICATIONS

Lisbonne, M. et al "Cutting edge: invariant V(alpha)14 NKT cells are required . . . " J. Immunol. (2003) vol. 171, pp. 1637-1641.*
Boniface, S. et al "Assessment of T lymphocyte cytokine production . . . " Clin. Exp. Allergy (2003) vol. 33, pp. 1238-1243.*
Haile, S. et al "Suppression of intermediate and late responses to antigen . . . " Euro. Respir. J. (1999) vol. 13, pp. 961-969.*
Gibson, P. "Monitoring the patient with asthma . . . " J. Allergy Clin. Immunol. (2000) vol. 106, No. 1, pp. 17-26.*
Ortaldo, Jr et al., "Disassociation of NKT stimulation, cytokine induction, and NK activation in vivo by the use of distinct TCR-binding ceramides," J. Immunol., Jan. 15, 2004, vol. 172, No. 2, 943-953.
Yang, JQ et al., "Immunoregulatory role of CD1d in the hydrocarbon oil-induced model of lupus nephritis," J Immunol, Aug. 15, 2003, vol. 171, No. 4, 2142-2153.

(Continued)

Primary Examiner — Leigh Maier
(74) Attorney, Agent, or Firm — Stradley Ronon Stevens & Young LLP

(57) ABSTRACT

Molecules that interact with the NKT cell antigen receptor and its counterpart antigen presenting molecule, but which inhibit the NKT cell immune function, are administered to a patient. Conditions of particular interest include the treatment of systemic lupus erythematosus (SLE), cancer, atherosclerosis, and allergic disease. In some embodiment of the invention, the inhibitory agent is an anergizing glycolipid, for example β-galactosylceramide. Pharmaceutical formulations of such glycolipids are provided, and find use in the treatment of diseases involving undesirable NKT cell activation.

12 Claims, 8 Drawing Sheets

(56) References Cited

OTHER PUBLICATIONS

Zeng, D., et al., "Activation of natural killer T cells in NZB/W mice induces Th1-type immune responses exacerbating lupus," J Clin Invest., Oct. 2003, vol. 112, No. 8, 1211-1222.
Galactocerebroside bovine derived, Sigma-Aldrich product catalogue, Jun. 2, 2011. URL,http://www.sigmaaldrich.com/catalog/ProductDetail.do?D7=0&N5=SEARCH_CONCAT_PNO%7CBRAND_KEY&N4=C4905%7CSIGMA&N25=0&QS=ON&F=SPEC.
Akbari, et al., "CD4+ invariant T-cell-receptor+ natural killer T cells in bronchial asthma," N Engl J Med., Mar. 16, 2006, 354(11), 1117-29.
Akbari et al., "Essential role of NKT cells producing IL-4 and IL-3 in the development of allergen-induced airway hyperreactivity," Nat Med., May 2003, 9(5) 582-8.
Anderson, G.P., "Endotyping asthma: new insights into key pathogenic mechanisms in a complex, heterogeneous disease," Lancet, Sep. 20, 2008, 372(9643) 1107-19.
Araujo, LM et al., Eur J Immunol, 2004, vol. 34, 327-335.
Bilenki et al., "Natural killer T cells contribute to airway eosinophilic inflammation induced by ragweed through enhanced IL-4 and eotaxin production," Eur J. Immunol, Feb. 2004, 34(2), 345-54.
Blumberg et al., "Expression of a nonpolymorphic MHC class I-like molecule, CD1D, by human intestinal epithelial cells," The Journal of Immunology, 1991, 147, 2518-2524.
Brown et al., "Beta 2-microglobulin-dependent NK1.1+ T cells are not essential for T helper cell 2 immune responses," J Exp Med, Oct. 1, 1996, 184(4), 1295-1304.
Chang, Y. et al., "The synthesis and biological characterization of a ceramide library," Journal of the American Chemical Society, 2002, 124(9), 1856-1857.
Kallinich et al., "T-cell co-stimulatory molecules: their role in allergic immune reactions," Eur Respir J., Jun. 2007, 29(6), 1246-55.
Kim et al., "Asthma is induced by intranasal coadministration of allergen and natural killer T-cell ligand in a mouse model," J Allergy Clin Immunol, Dec. 2004, 114(6), 1332-8.
Leckie et al., "Effects of an interleukin-5 blocking monoclonal antibody on eosinophils, airway hyper-responsiveness, and the late asthmatic response," Lancet, Dec. 23-30, 2000, 356(9248), 2144-8.
Linden, A., "Role of Interleukin-17 and the Neutrophil in Asthma," Int Arch Allergy Immunol, Nov. 2001, 126(3), 179-84. (abstract only).
Louis et al., "The relationship between airways inflammation and asthma severity," Am J Respir Crit Care Med, Jan. 2000, 161(1), 9-16.
Panja et al., "Adhesion molecules are expressed on intestinal epithelial cells but do not participate in T Cell interactions," Gastroenterology, 1991, 100:A606.
Park, J. et al., "Inhibitory activity of a ceramide library on interleukin-4 production from activated T cells," Bioorganic & Medicinal Chemistry, 2005, 13, 1589-2595.
Rhee, R.J. et al., Journal of Surgical Research, 2003, 115, 74-81.
Sachiko Miyake et al., "Potential of targeting natural killer T cells for the treatment of autoimmune diseases," Mod Rheumatology, 2004, 14, 279-284.
Tupin et al., "CD1d-dependent activation of NKT cells aggravates atherosclerosis," The Journal of Experimental Medicine, 2004, 199(3), 417-422.
Umetsu, D. et al., "Regulatory T cells control the development of allergic disease and asthma," J Allergy Clin Immunol., 2003, 112(3), 480-487.
Vijayanand et al., "Invariant natural killer T cells in asthma and chronic obstructive pulmonary disease," N Engl J Med., Apr. 5, 2007, 356(14), 1410-22.
Wenzel et al., "Effect of an interleukin-4 variant on late phase asthmatic response to allergen challenge in asthmatic patients: results of two phase 2a studies," Lancet, Oct. 20, 2007, 370(9596), 1422-31.
Williams et al., "Mast cells can amplify airway reactivity and features of chronic inflammation in an asthma model in mice," J Exp Med., Aug. 7, 2000, 192(3), 455-62.
Yoshimoto, T. et al., J Exp Med, 2003, 197, 997-1005.
Zeng et al., J Immunol, 2000, 164, 5000-4.
Zhang et al., "Beta 2-microglobulin-dependent T cells are dispensable for allergen-induced T helper 2 responses," J Exp Med., Oct. 1, 1996, 184(4), 1507-1512.
Humbles, A., et al., "A Critical Role for Eosinophils in Allergic Airways Remodeling", Science (2004), vol. 205, pp. 1776-1779.
Korsgren, M., et al., "Natural Killer Cells Determine Development of Allergen-induced Eosinophilic Airway Inflammation in Mice", J. Exp. Med. (1999), vol. 189, pp. 553-562.
Mehlhop, P., et al., "Allergen-induced Bronchial Hyperreactivity and Eosinophilic Inflammation Occur in the Absence of IgE in a Mouse Model of Asthma", Proc. Natl. Acad. Sci. USA (1997), vol. 94, pp. 1344-1349.
Hogan, S., et al., "Aeroallergen-induced Eosinophilic Inflammation, Lung Damage, and Airways Hyperreactivity in Mice Can Occur Independently if IL-4 and Allergen-Specific Immunoglobulins", J. Clin. Invest. (1997), vol. 99, No. 6, pp. 1329-1339.
Brightling, C.E., et al., "Eosinophilis in Asthma and Airway Hyperresponsiveness", Am. J. Resp. Crit. Care Med. (2004), vol. 169, pp. 131-133.

* cited by examiner

METHODS FOR RELIEVING ASTHMA-ASSOCIATED AIRWAY HYPERRESPONSIVENESS

CROSS-REFERENCE

This application is a divisional application of U.S. application Ser. No. 11/266,033, filed on Nov. 2, 2005, which claims the benefit of U.S. Provisional Application No. 60/706,548, filed Aug. 8, 2005 and U.S. Provisional Application No. 60/624,568, filed Nov. 2, 2004, which applications are incorporated herein by reference.

STATEMENT AS TO FEDERALLY SPONSORED RESEARCH

This invention was made with the support of the United States government under Grant NIH-AI-40093 awarded by the National Institutes of Health.

BACKGROUND OF THE INVENTION

This invention was made with Government support under grant NIH-AI-40093 awarded by the National Institutes of Health. The Government has certain rights in this invention.

NKT cells constitute a unique subpopulation of T lymphocytes, which are highly conserved in both human and murine species. NKT cells express some NK-specific surface markers, such as the C-type lectin NKRP-1A, thereby sharing some properties with classical NK cells. NKT cells also express a semi-invariant T cell receptor, consisting in humans of an invariant V$\alpha$24J$\alpha$Q rearrangement paired preferentially with a variable V$\beta$11 chain. In the mouse, NKT cells express an invariant V$\alpha$14J$\alpha$281 rearrangement paired with variable V$\beta$8, V$\beta$7, or V$\beta$2. In terms of co-receptor expression, invariant NKT cells belong either to the single positive CD4+ or the double negative CD4–CD8–TCR$\alpha$/$\beta$+ subset of lymphocytes.

Although natural ligands of NKT cells have not yet been identified, these cells are activated when their TCR recognizes glycosylceramides derived from marine sponges, presented by CD1d. Although this class of $\alpha$-glycosylated ceramides are not detectable in mammals, they may share critical structural features with natural CD1d-ligands, suggesting that NKT cells recognize antigens containing a hydrophobic (lipid) and a hydrophilic moiety.

The biological role of NKT cells is not well defined. In response to activation through their T cell receptor, NKT cells have been shown to secrete large amounts of both interferon-$\gamma$ (IFN-$\gamma$) and interleukin-4 (IL-4) (see, for example, Hong et al. (1999) Immunol Rev. 169:131; and Singh et al. (1999) J Immunol 163:2373). After repeated activation, NKT cells become polarized cells that produce predominantly IL-4.

It has also been suggested that NKT cells serve an immunoregulatory function in the control of susceptibility to certain autoimmune diseases. For example, in some disease models, transfer of NKT cells to disease-susceptible recipients prevents the development of autoimmune disease, and it has been suggested that activation of NKT cells could provide for therapeutic intervention for the immunoregulation of autoimmune disease (Sharif et al. (2002) J. Mol. Med. 80:290-300) by polarizing conventional T cells toward IL-4 production. It has also been reported that NKT cells and IL-13 (possibly produced by NKT cells) can down-regulate cytotoxic T lymphocyte-mediated tumor immunosurveillance (Terabe et al. (2000) Nat Immunol 1(6):515-20).

However, it has also been reported that activation of NKT cells augments Th1-type immune responses and autoantibody secretion that contribute to lupus development in adult NZB/W mice (Zeng et al. (2003) J Clin Invest 112:1211).

The role of NKT cells in human clinical conditions is of great interest. There is a high level of conservation between species for the NKT cell system. $\alpha$-Galactosylceramide can stimulate both murine and human NKT cells, and both mouse and human CD1d molecules are able to present $\alpha$-GalCer to NKT cells from either species, indicating the relevance of animal studies for human clinical trials. Methods of manipulating NKT cell responses are provided by the present invention.

SUMMARY OF THE INVENTION

Methods and compositions are provided for inhibiting ("anergizing") NKT cell function thereby inhibiting NK T cell activation by synthetic or natural agonists. Molecules that interact with the NKT cell antigen receptor and its presenting molecule, e.g. CD1, such that the immune function of the NK T cell is inhibited, are administered to a patient and act to inhibit NKT cell activation. Conditions of particular interest include the treatment of systemic lupus erythematosus (SLE), and allergic diseases, including asthma. In some embodiment of the invention, the inhibitory agent is an anergizing glycolipid that downregulates the NK T cell antigen receptors. Such glycolipids may comprise a $\beta$ linkage between the sugar and lipid moieties, for example ($\beta$-galactosylceramide. Pharmaceutical formulations of such glycolipids are provided, and find use in the treatment of diseases involving undesirable NKT cell activation.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
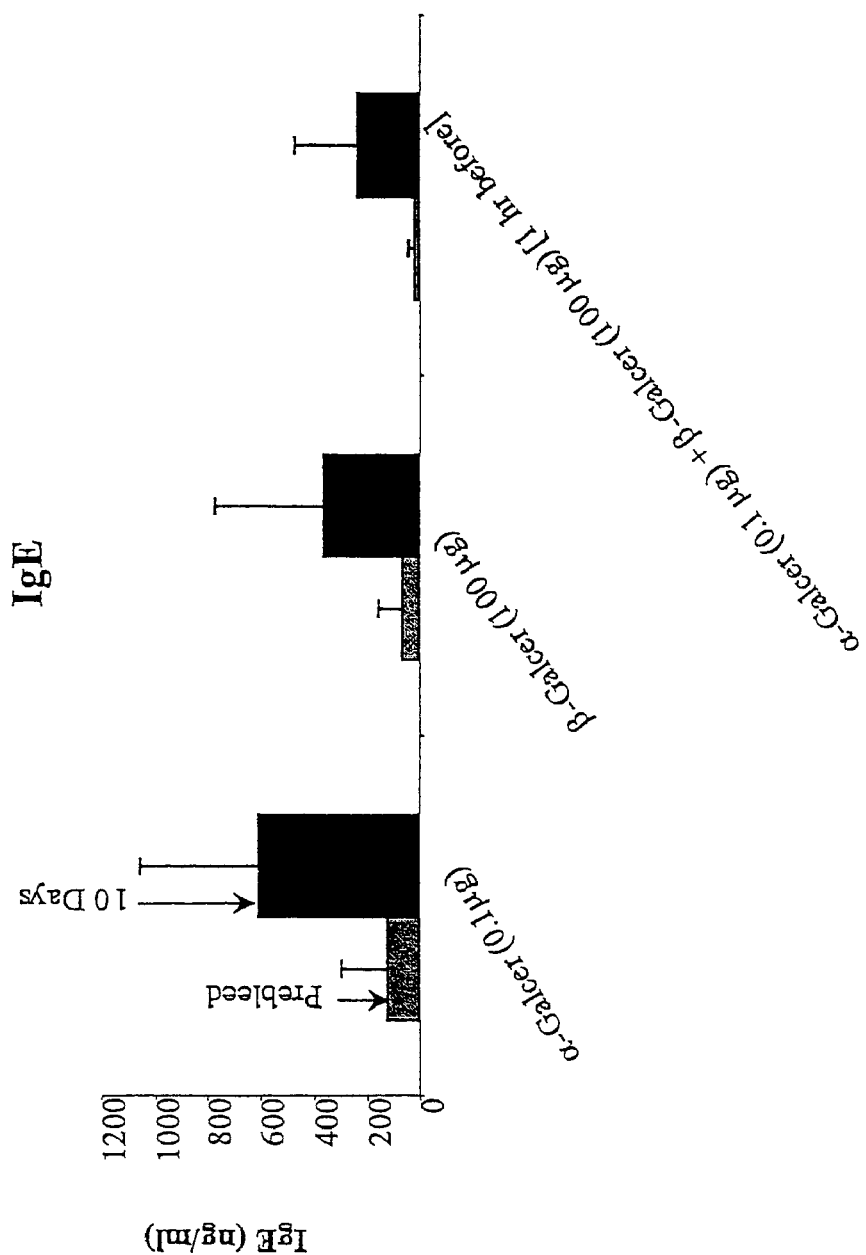
FIGS. 1A-1D. Treatment with $\beta$-Galcer reduces the effects of NKT cell activation in vivo, including expression of IFN-$\gamma$, IL-4, and IgE synthesis. Synthesis of IgG2c is not affected.
Figure 1B:
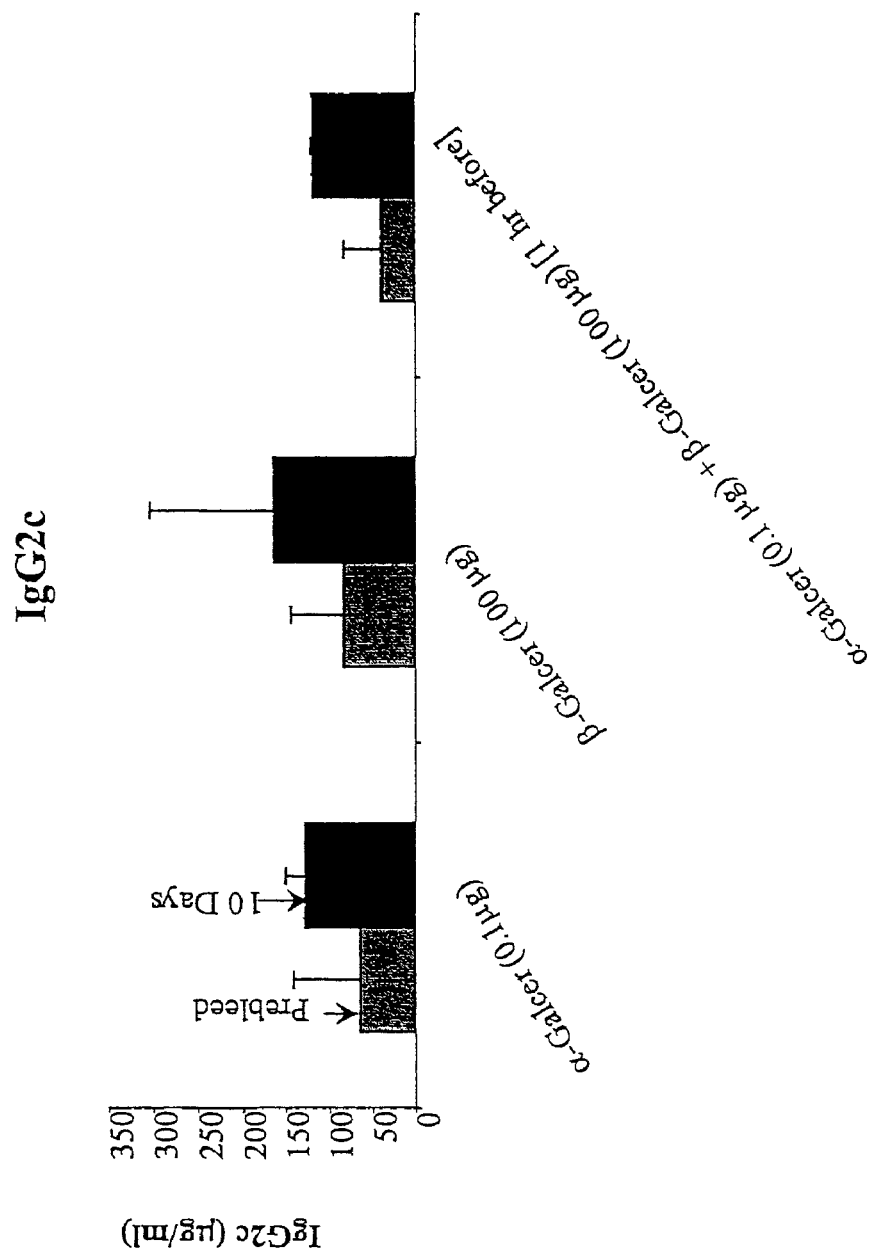
Figure 1C:
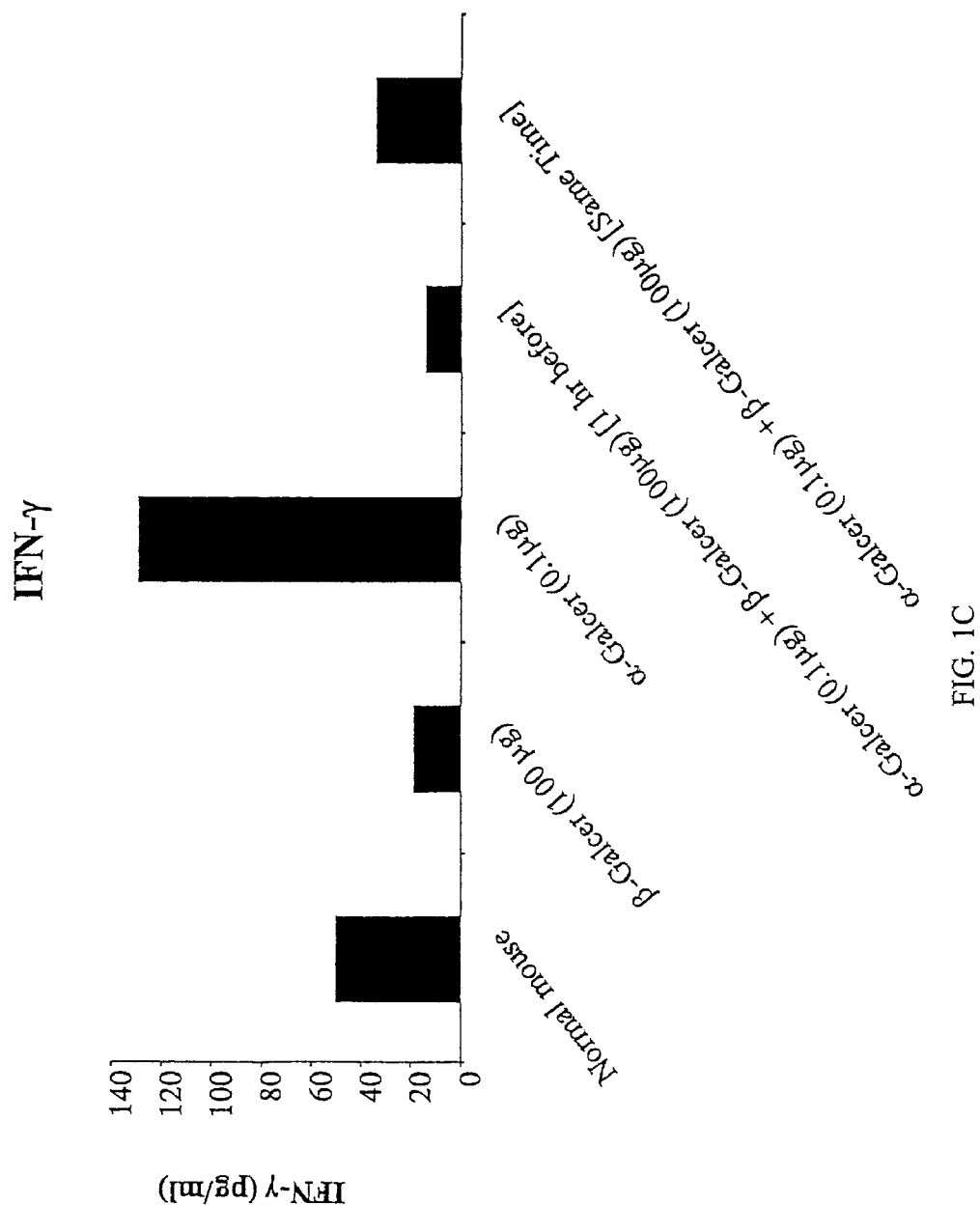
Figure 1D:
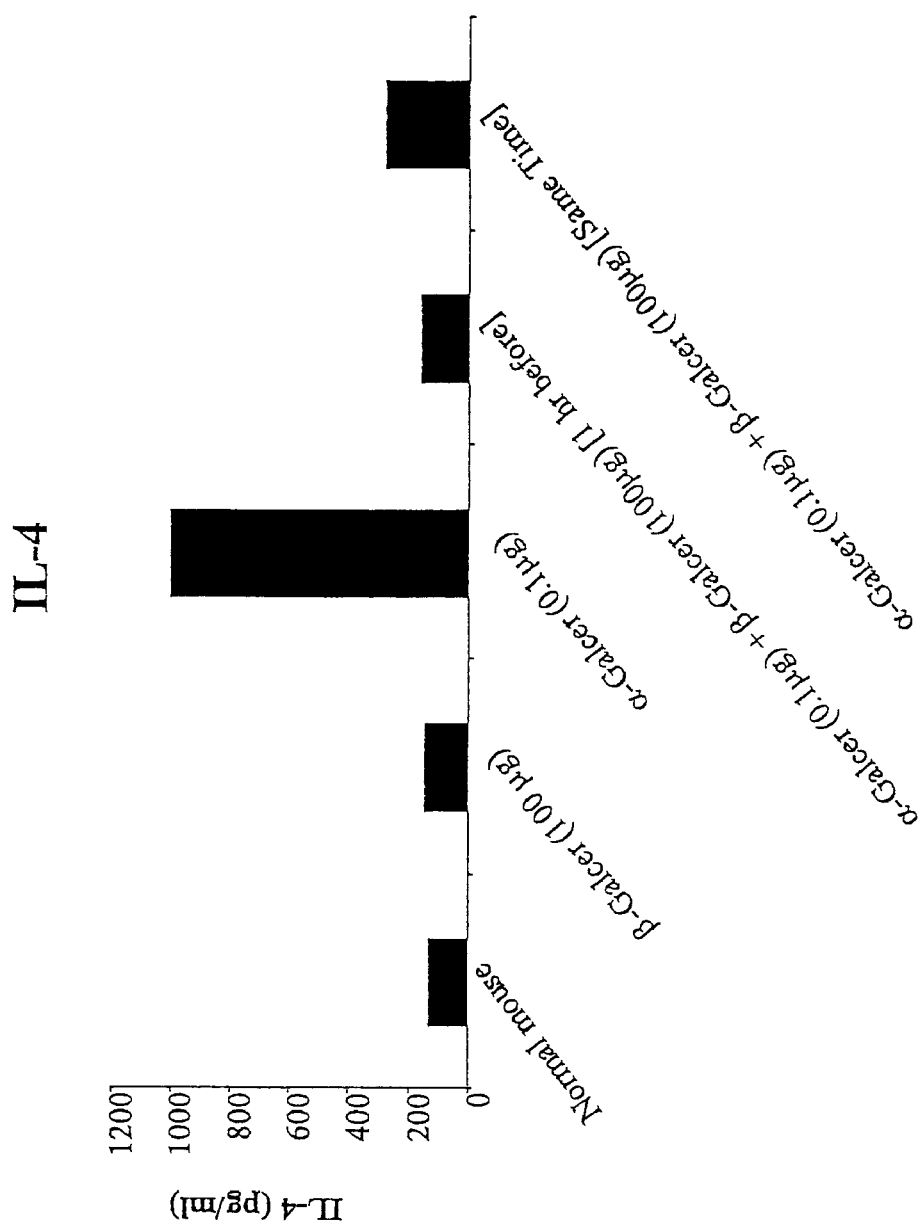

Methods and compositions are provided for inhibiting NKT cell immune function, particularly in the treatment of allergic diseases, or SLE. Molecules that specifically interact with the NKT cell antigen receptor and its presenting molecule, e.g. CD1, and that inhibit the immune function of the NKT cells are administered to a patient, and act to inhibit NKT cell activation response to agonists. In some embodiment of the invention, the blocking agent is an anergizing glycolipid that downregulates the NK T cell antigen receptors. Such glycolipids may comprise a β linkage between the sugar and lipid moieties, for example β-galactosylceramide.

The term "treatment" or "treating" means any treatment of a disease in a mammal, including, without limitation, allergic diseases, e.g. asthma; SLE; etc., in human and animal models. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; and/or relieving the disease, that is, causing the regression of clinical symptoms by administration of a protective composition after their initial appearance.

It will be understood that in human medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "treatment," as used herein, is meant to include "prophylaxis."

The term "effective amount" means a dosage sufficient to provide treatment for the disease state being treated. This will vary depending on the patient, the disease and the treatment being effected. NKT cell inhibitory agents are used for the treatment of disease; and can be used in co-formulations, e.g. as a steroid sparing agent to facilitate use of lower prednisone or hydrocortisone dose.

In vivo activity for the treatment of disease may be demonstrated by testing an inhibitory agent in an animal model, for example an induced asthma model in animals; or one of several strains of inbred mice with inherited lupus-like disease, observing for the appearance of ANA production, pathogenic anti-ds DNA antibodies, immune complex glomerulonephritis, lymphadenopathy, and abnormal B and T cell function mimicking the human situation, in control and treated groups. Human clinical efficacy is demonstrated in clinical trials, employing methodology known to those skilled in the art.

I. Definitions

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a construct" includes a plurality of such constructs and reference to "the cell" includes reference to one or more cells and equivalents thereof known to those skilled in the art, and so forth. All technical and scientific terms used herein have the same meaning as commonly understood to one of ordinary skill in the art to which this invention belongs unless clearly indicated otherwise.

Allergy is an increased tendency to IgE-based sensitivity resulting in production of specific IgE antibody to an immunogen including, for example, insect venom, dust mites, pollens, molds, animal dander, food antigens, or latex. Allergic responses are antigen specific and are characterized by the production of Th2-type cytokines such as, for example, IL-4, IL-5, IL-10, IL-13, etc. Sensitization to a particular allergen occurs in genetically predisposed people after exposure to antigen; cigarette smoke and viral infections may assist in the sensitization process.

Included in this group are those with asthma associated allergies, who develop clinical disease ranging from trivial rhinitis to life-threatening asthma. After sensitization, continuing exposure to allergens leads to a significant increase in the prevalence of asthma. Once sensitization has occurred, re-exposure to allergen is a risk factor for exacerbation of asthma. Effective management of allergic asthma has typically required pharmacologic therapy and allergen avoidance. The specific physiological effects of asthma associated with allergies include airway inflammation, eosinophilia and mucus production, and production of IL-4 and antigen-specific IgE.

Mast cells, derivatives of hematopoietic precursor cells that undergo their terminal stages of differentiation/maturation in the peripheral tissues in which they reside, express cell surface receptors (FcRI) that permit them to bind the Fc portion of IgE with high affinity. Such IgE-sensitized mast cells, upon encounter with specific antigen that is recognized by their FcRI-bound IgE, secrete a broad panel of bioactive mediators, including: preformed mediators that are stored in the cell's cytoplasmic granules, e.g. histamine, heparin, and neutral proteases, newly synthesized lipid products, e.g. prostaglandin D2 and leukotriene C4, and diverse cytokines. Many of these potentially mast cell-derived mediators can promote reversible airway obstruction, bronchial hyperreactivity, and/or airway inflammation.

However, additional cell types, including eosinophils and Th2 lymphocytes, both of which are well represented in the chronic inflammatory infiltrates in the airways of patients with asthma, also can produce cytokines or other mediators that may contribute to many of the features of the disease. The FcRI, which was once thought to be restricted to tissue mast cells and basophils, is also expressed on the surface of monocytes, circulating dendritic cells, Langerhans' cells, and eosinophils, thus implicating these cells as additional potential sources of mediators in various IgE-dependent inflammatory responses. (For a review, see Galli (1997) J. E. M. 186:343-347, which disclosure and the references cited therein are herein incorporated by reference)

Allergens are immunogenic compounds that cause Th2-type T cell responses and IgE B cell responses in susceptible individuals. The specific allergen may be any type of chemical compound such as, for example, a polysaccharide, a fatty acid moiety, a protein, etc. Allergens include antigens found in foods such as fruits (e.g., melons, strawberries, pineapple and other tropical fruits), peanuts, peanut oil, other nuts, milk proteins, egg whites, shellfish, tomatoes, etc.; airborne antigens such as grass pollens, animal danders, house mite feces, etc.; drug antigens such as penicillins and related antibiotics, sulfa drugs, barbituates, anticonvulsants, insulin preparations (particularly from animal sources of insulin), local anesthetics (e.g., Novocain), and iodine (found in many X-ray contrast dyes); insect venoms and agents responsible for allergic dermatitis caused by blood sucking arthropods such as Diptera, including mosquitos (*Anopheles* sp., *Aedes* sp., *Culiseta* sp., *Culex* sp), flies (*Phlebotomus* sp., *Culicoides* sp.) particularly black flies, deer flies and biting midges, ticks (*Dermmacenter* sp., *Ornithodoros* sp., *Otobius* sp), fleas (e.g., the order *Siphonaptera*, including the genera *Xenopsylla, Pulex* and *Ctenocephalides felis felis*); and latex.

Anaphylactic allergens are those antigens that pose a risk of anaphylactic reaction in hypersensitive individuals. Anaphylaxis is an acute, systemic allergic reaction that occurs after an individual has become sensitized to an antigen. Anaphylaxis is associated with the production of high levels of IgE antibodies and with the release of histamines, which cause muscle contractions, constriction of the airways, and dilation of blood vessels. Symptoms of anaphylactic reactions include hives, generalized itching, nasal congestion, wheezing, difficulty breathing, cough, cyanosis, lightheadedness, dizziness, confusion, slurred speech, rapid pulse, palpitations, nausea and vomiting, abdominal pain or cramping, skin redness or inflammation, nasal flaring, intercostal retractions, etc.

Asthma, as defined herein, is a syndrome, typically characterized by the three cardinal features of intermittent and reversible airway obstruction, airway hyperresponsiveness, and airway inflammation, which may arise as a result of interactions between multiple genetic and environmental factors. Asthma is characterized by the presence of cells such as eosinophils, mast cells, basophils, and $CD25^+$ T lymphocytes in the airway walls. There is a close interaction between these cells, because of the activity of cytokines, which have a variety of communication and biological effector properties. Chemokines attract cells to the site of inflammation and cytokines activate them, resulting in inflammation and damage to the mucosa. With chronicity of the process, secondary changes occur, such as thickening of basement membranes and fibrosis. The disease is characterized by increased airway hyperresponsiveness to a variety of stimuli, and airway inflammation. A patient diagnosed as asthmatic will generally have multiple indications over time, including wheezing, asthmatic attacks, and a positive response to methacholine challenge, i.e., a $PC_{20}$ on methacholine challenge of less than about 4 mg/ml. Guidelines for diagnosis may be found, for example, in the National Asthma Education Program Expert Panel Guidelines for Diagnosis and Management of Asthma, National Institutes of Health, 1991, Pub. No. 91-3042.

SLE. Systemic lupus erythematosus (SLE) is an autoimmune disease characterized by polyclonal B cell activation, which results in a variety of anti-protein and non-protein autoantibodies (see Kotzin et al. (1996) Cell 85:303-306 for a review of the disease). These autoantibodies form immune complexes that deposit in multiple organ systems, causing tissue damage. SLE is a difficult disease to study, having a variable disease course characterized by exacerbations and remissions. For example, some patients may demonstrate predominantly skin rash and joint pain, show spontaneous remissions, and require little medication. The other end of the spectrum includes patients who demonstrate severe and progressive kidney involvement (glomerulonephritis) that requires therapy with high doses of steroids and cytotoxic drugs such as cyclophosphamide.

Multiple factors may contribute to the development of SLE. Several genetic loci may contribute to susceptibility, including the histocompatibility antigens HLA-DR2 and HLA-DR3. The polygenic nature of this genetic predisposition, as well as the contribution of environmental factors, is suggested by a moderate concordance rate for identical twins, of between 25 and 60%.

Many causes have been suggested for the origin of autoantibody production. Proposed mechanisms of T cell help for anti-dsDNA antibody secretion include T cell recognition of DNA-associated protein antigens such as histones and recognition of anti-DNA antibody-derived peptides in the context of class II MHC. The class of antibody may also play a factor. In the hereditary lupus of NZB/NZW mice, cationic IgG2a anti-double-stranded (ds) DNA antibodies are pathogenic. The transition of autoantibody secretion from IgM to IgG in these animals occurs at the age of about six months, and T cells may play an important role in regulating the IgG production.

Disease manifestations result from recurrent vascular injury due to immune complex deposition, leukothrombosis, or thrombosis. Additionally, cytotoxic antibodies can mediate autoimmune hemolytic anemia and thrombocytopenia, while antibodies to specific cellular antigens can disrupt cellular function. An example of the latter, is the association between anti-neuronal antibodies and neuropsychiatric SLE.

NKT cells constitute a lymphocyte subpopulation that are abundant in the thymus, spleen, liver and bone marrow and are also present in the lung. They develop in the thymus from the $CD4^+CD8^+$ progenitor cells and circulate in the blood, have distinctive cytoplasmic granules, and can be functionally identified by their ability to kill certain lymphoid tumor cell lines in vitro without the need for prior immunization or activation. The mechanism of NKT cell killing is the same as that used by the cytotoxic T cells generated in an adaptive immune response; cytotoxic granules are released onto the surface of the bound target cell, and the effector proteins they contain penetrate the cell membrane and induce programmed cell death.

NKT cells express surface markers that are characteristic of both natural killer cells (such as NK1.1 and CD161) and conventional T cells (such as TCRs). Several NKT cells recognize glycolipid antigens presented by the non-polymorphic major histocompatibility complex (MHC) class I-like protein CD1d and express an invariant TCR in mice.

NKT cell antigen receptor. The receptor for antigen NKT cells is an $\alpha$:$\beta$ T-cell receptor composed of two protein chains, T-cell receptor $\alpha$ and T-cell receptor $\beta$. As with the receptor on conventional T cells, it is believed that the NKT cell receptor does not recognize antigen in its native state. Conventional T cells recognize a composite ligand of a peptide antigen bound to an MHC molecule. It is believed that the presenting molecule for the NKT cell antigen receptor is CD1d, which is often associated with glycolipids, rather than peptide fragments. It is believed that, analogous to other MHC class I molecules, bound antigen is sandwiched between the two $\alpha$-helical segments of CD1d. The T-cell receptor interacts with this compound ligand, making contacts with both CD1d and with the antigen.

The amino acid sequences of T-cell receptor show that both chains have an amino-terminal variable (V) region with homology to an immunoglobulin V domain, a constant (C) region with homology to an immunoglobulin C domain, and a short hinge region containing a cysteine residue that forms the interchain disulfide bond. Each chain spans the lipid bilayer by a hydrophobic transmembrane domain, and ends in a short cytoplasmic tail.

The TCR$\alpha$ locus contains V and J gene segments (V$\alpha$ and J$\alpha$). The TCR$\beta$ locus contains D gene segments in addition to V$\beta$ and J$\beta$ gene segments. The third hypervariable loops (CDR3s) of the T-cell receptor $\beta$ and $\beta$ chains, to which the D and J gene segments contribute, form the center of the antigen-binding site of a T-cell receptor; the periphery of the site consists of the equivalent of the CDR1 and CDR2 loops, which are encoded within the germline Vα and Vβ gene segments.

The T cell receptor of NKT cells consisting in humans of an invariant Vα24JαQ rearrangement paired preferentially with a variable Vβ11 chain. In the mouse, NKT cells express an invariant Vα14Jα281 rearrangement paired with variable Vβ8, Vβ7, or Vβ2.

CD1: CD1 is a nonpolymorphic, class I MHC-like, non-MHC encoded molecule that may be found non-covalently associated with $\beta_2$-microglobulin ($\beta_2$m). In humans, five isoforms of CD1 have been identified (CD1a, b, c, d and e), and human B cells are known to express CD1c and CD1d. In mice, only the CD1d isoform has been identified. CD1 molecules have been demonstrated to be antigen-presenting molecules for glycolipid and hydrophobic peptides. In some embodiments of the invention, the CD1 isoform is CD1d, which interacts with the NKT cell antigen receptor.

The human and mouse isoforms of CD1 have been cloned and characterized as to their sequence. The sequence of human CD1a may be found in Genbank, accession number M28825. The sequence of CD1b may be found in PIR1 section of the Protein Sequence Database, release 64.00, 31 Mar. 2000, accession numbers B39957; B45801; and 179470 (Martin et al. (1987) Proc Natl Acad Sci USA 84(24):9189-93). The sequence of CD1c may be found in PIR1, accession numbers C45801; C39957; and I79472 (Aruffo and Seed (1989) J. Immunol. 143:1723-1730). Human CD1d may be found in Genbank, accession number J04142 (Balk et al. (1989) Proc. Natl. Acad. Sci. U.S.A. 86 (1), 252-256). Human CD1e sequence may be found in Genbank, accession number X14975, X15110 (Calabi et al. (1989) Eur. J. Immunol. 19 (2), 285-292).

For the purposes of the present invention, the anergizing agent will bind to the CD1 protein present on antigen presenting cells of the patient being treated. That is, for human therapy the anergizing agent will bind human CD1; and the like. Because CD1 is not highly polymorphic a patient will generally express the wild-type protein as described above, although there may be exceptions where a patient expresses a variant form of the protein.

Agents may specifically bind to one or more of the human CD1 isoforms, particularly isoforms expressed on antigen presenting cells, e.g. CD1d. In an alternative embodiment, a cross-reactive anergizing agent that recognizes common epitopes on all CD1 isoforms; or a cocktail of isoform specific agents; is used to generally bind all CD1 isoforms present in the patient.

NKT cell inhibitory agents: are molecules that interfere with the activation of NKT cells through their antigen receptor, for example by competitive or non-competitive binding to the extracellular domain of CD1, or to the T cell antigen receptors, or that block the presentation of an activating antigen. Usually the binding affinity of the inhibitory agent will be at least about 100 μM. Inhibitory agents may be peptides, lipids, e.g. glycolipids, phospholipids, etc., either alone or in combination with a peptide; small organic molecules, peptidomimetics, soluble T cell receptors; or the like. Glycolipids are a preferred blocking agent.

In one embodiment of the invention, the NKT cell inhibitory agent is an anergizing glycolipid. Glycolipids of interest have the general structure:

G-L where L is a lipid and G is a saccharide, which may be a hexose or a pentose, and may be a mono, di-, tri-, oligo, or polysaccharide, or a derivative thereof. Sugars of interest include allose, altrose, glucose, mannose, gulose, idose, galactose, talose, fructose, maltose, lactose, and sucrose. The linkage between the sugar and the lipid may be at any of the O atoms, usually at position 1, 2, 3 or 4, more usually at position 1. The linkage may be in the alpha or beta configuration, in some specific embodiments the linkage is in the beta configuration. Lipids of interest include ceramides, with an acyl chain and a sphingosine chain.

For example, the NKT cell inhibitory agent may have the structure:

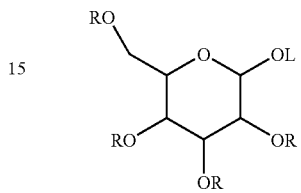

where L is a lipid, and R is selected from the group consisting of H, a pentose sugar, a hexose sugar, an oligo- or polysaccharide; or an alkyl, aryl or alkenyl group, such as a C1 to C6 lower alkyl, which alkyl is optionally substituted, which substituent may include, without limitation, an alkyl, aryl, alkenyl, aralkyl, aralkenyl, cycloalkyl, cycloalkylalkyl or cycloalkylalkenyl group; and may contain one or more N, S or O heteroatoms. Each of the O atoms may be in the α or β orientation, e.g. glucose, galactose, mannose, etc.

In one embodiment of the invention, G has the structure:

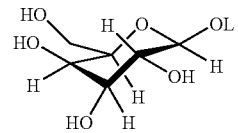

where G is a galactose, and where the linkage to L (as shown) is at the 1 position, in the α or β configuration.

A number of lipids find use as L, including C8 to C30 fatty acids, long chain secondary alcohols, long chain amino alcohols, amides of fatty acids with long-chain di- or trihydroxy bases; and the like. For example, a glycosyl moiety (one or several units) may be linked to one hydroxyl group of a fatty alcohol or hydroxy fatty alcohol, or to a carbonyl group of a fatty acid. Examples of suitable lipids include ceramides, sphingomyelin, cerebrosides, and the like, including sphiongosine, dihydrosphingosine, C20-dihydrosphingosine, phytosphingosine, C20-phytosphingosine, dehydrophytosphingosine, sphingadienine, etc.

Branch-chain sphingoid bases have been described in some marine invertebrates. Thus, a base with a branched C19 alkyl chain and three double bonds, 2-amino-9-methyl-4,8,10-octadecatriene-1,2-diol, was shown to be present in glucosylceramide from starfish (Irie A et al., J Biochem 1990, 107, 578) and in sphingomyelin from squid nerve (Ohashi et al., J Lipid Res 2000, 41, 1118). A branched base with two double bonds has been found in cerebrosides from a sea anemone (Karlsson et al., Biochim Biophys Acta 1979, 574, 79) and from mycelia of a fungus (Kawai et al., J Lipid Res 1985, 26, 338).

Ceramides are amides of fatty acids with long-chain di- or trihydroxy bases, the commonest in animals being sphingosine and in plants phytosphingosine. The acyl group of ceramides is generally a long-chain saturated or monounsaturated fatty acid. The most frequent fatty acids found in animal ceramides are 18:0, 24:0 and 24:1 (n-9), long-chain hydroxy fatty acids are also found.

In one embodiment, the NKT cell inhibitor has the structure:

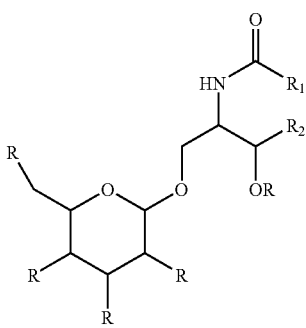

where $R_1$ and $R_2$ may be the same or different, and are independently selected from an alkyl or alkenyl of from about 8 to 30 carbons, which may be linear or branched, usually linear, and usually not more than 0, 1, 2 or 3 unsaturated bonds, which chain may be optionally substituted or phosphorylated or sulfated; or a derivative thereof, including esters and the like; and Each R may be the same or different, and are independently selected from the group consisting of H, OH, an ether of a lower alkyl aryl or alkenyl group, which alkyl is optionally substituted, which substituent may include, without limitation, an alkyl, aryl, alkenyl, aralkyl, aralkenyl, cycloalkyl, cycloalkylalkyl or cycloalkylalkenyl group; and may contain one or more N, S or O heteroatoms, an O linked pentose sugar, an O linked hexose sugar, a O linked oligo- or polysaccharide; or an alkyl, aryl or alkenyl group, such as a C1 to C6 lower alkyl, which alkyl is optionally substituted, which substituent may include, without limitation, an alkyl, aryl, alkenyl, aralkyl, aralkenyl, cycloalkyl, cycloalkylalkyl or cycloalkylalkenyl group; and may contain one or more N, S or O heteroatoms. Each of the R atoms may be in the α or β orientation, e.g. glucose, galactose, mannose, etc.

In one embodiment, the NKT cell inhibitor has the structure:

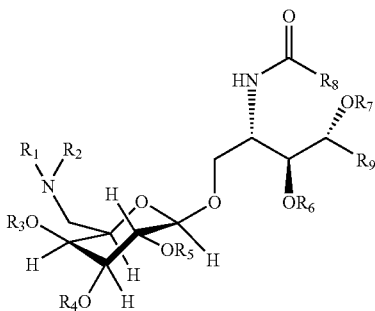

wherein, $R_1$ is: (i) hydrogen; or (ii) —$SO_2R_{10}$, wherein $R_{10}$ is: halo; hydroxy; $OR_{11}$; $OR_{12}$; amino; $NHR_{11}$; $N(R_{11})_2$; $NHR_{12}$; $N(R_{12})_2$; aralkylamino; or $C_1$-$C_{12}$ alkyl optionally substituted with halo, hydroxy, oxo, nitro, $OR_{11}$, $OR_{12}$, acyloxy, amino, $NHR_{11}$, $N(R_{11})_2$, $NHR_{12}$, $N(R_{12})_2$, aralkylamino, mercapto, thioalkoxy, $S(O)R_{11}$, $S(O)R_{12}$, $SO_2R_{11}$, $SO_2R_{12}$, $NHSO_2R_{11}$, $NHSO_2R_{12}$, sulfate, phosphate, cyano, carboxyl, $C(O)R_{11}$, $C(O)R_{12}$, $C(O)OR_{11}$, $C(O)NH_2$, $C(O)NHR_{11}$, $C(O)N(R_{11})_2$, $C_3$-$C_{10}$ cycloalkyl containing 0-3 $R_{13}$, $C_3$-$C_{10}$ heterocyclyl containing 0-3 $R_{13}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl containing 0-3 $R_{14}$, or heteroaryl containing 0-3 $R_{14}$; or $C_3$-$C_{10}$ cycloalkyl, $C_3$-$C_{10}$ heterocyclyl, $C_5$-$C_{10}$ cycloalkenyl, or $C_5$-$C_{10}$ heterocycloalkenyl optionally substituted with one or more halo, hydroxy, oxo, $OR_{11}$, $OR_{12}$, acyloxy, nitro, amino, $NHR_{11}$, $N(R_{11})_2$, $NHR_{12}$, $N(R_{12})_2$, aralkylamino, mercapto, thioalkoxy, $S(O)R_{11}$, $S(O)R_{12}$, $SO_2R_{11}$, $SO_2R_{12}$, $NHSO_2R_{11}$, $NHSO_2R_{12}$, sulfate, phosphate, cyano, carboxyl, $C(O)R_{11}$, $C(O)R_{12}$, $C(O)OR_{11}$, $C(O)NH_2$, $C(O)NHR_{11}$, $C(O)N(R_{11})_2$, alkyl, haloalkyl, $C_3$-$C_{10}$ cycloalkyl containing 0-3 $R_{13}$, $C_3$-$C_{10}$ heterocyclyl containing 0-3 $R_{13}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl heteroaryl containing 0-3 $R_{14}$, or $C_6$-$C_{20}$ heteroaryl containing 0-3 $R_{14}$; or $C_2$-$C_6$ alkenyl, $C_2$-$C_6$ alkynyl, aryl, or heteroaryl optionally substituted with one or more halo, hydroxy, $OR_{11}$, $OR_{12}$, acyloxy, nitro, amino, $NHR_{11}$, $N(R_{11})_2$, $NHR_{12}$, $N(R_{12})_2$, aralkylamino, mercapto, thioalkoxy, $S(O)R_{11}$, $S(O)R_{12}$, $SO_2R_{11}$, $SO_2R_{12}$, $NHSO_2R_{11}$, $NHSO_2R_{12}$, sulfate, phosphate, cyano, carboxyl, $C(O)R_{11}$, $C(O)R_{12}$, $C(O)OR_{11}$, $C(O)NH_2$, $C(O)NHR_{11}$, $C(O)N(R_{11})_2$, alkyl, haloalkyl, $C_3$-$C_{10}$ cycloalkyl containing 0-3 $R_{13}$, $C_3$-$C_{10}$ heterocyclyl containing 0-3 $R_{13}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl containing 0-3 $R_{14}$, or $C_6$-$C_{20}$ heteroaryl containing 0-3 $R_{14}$; or (iii) —$C(O)R_{10}$, wherein $R_{10}$ is defined as above; or (iv) —$C(R_{10})_2(R_{15})$, wherein $R_{10}$ is defined as above; $R_{15}$ is hydrogen, $R_{10}$, or $R_{15}$ and $R_2$ taken together forms a double bond between the carbon and nitrogen atoms to which they are attached; or (v) $R_1$ and $R_2$ taken together forms a heterocyclyl of 3-10 ring atoms optionally substituted with $R_{10}$; $R_2$ is hydrogen, or $R_2$ and $R_{15}$ taken together forms a double bond between the carbon and nitrogen atoms to which they are attached; or $R_2$ and $R_1$ taken together forms a heterocyclyl of 3-10 ring atoms optionally substituted with $R_{10}$;

$R_3$, $R_4$, $R_5$, $R_6$, and $R_7$ are each independently hydrogen, $C_1$-$C_6$ alkyl, $C_6$-$C_{12}$ aralkyl, or $C_1$-$C_6$ acyl; $R_8$ is —$(CH_2)_xCH_3$, $R_9$ is a linear or branched $C_3$-$C_{100}$ alkyl; $R_{11}$ is $C_1$-$C_{20}$ alkyl optionally substituted with halo, hydroxy, alkoxy, amino, alkylamino, dialkylamino, sulfate, or phosphate; $R_{12}$ is aryl optionally substituted with halo, haloalkyl, hydroxy, alkoxy, nitro, amino, alkylamino, dialkylamino, sulfate, or phosphate; Each $R_{13}$ is independently halo, haloalkyl, hydroxy, alkoxy, oxo, amino, alkylamino, dialkylamino, sulfate, or phosphate; Each $R_{14}$ is independently halo, haloalkyl, hydroxy, alkoxy, nitro, amino, alkylamino, dialkylamino, sulfate, or phosphate; and X is 1-100.

Referring to the formula above, a subset of compounds described above are those in which X is 24 and $R_9$ is n-tetradecyl.

Other suitable substituents are described in PCT/US2003/008530, which is incorporated herein by reference. PCT/US2003/008530 is directed to the α-form of the compounds, however, it is intended herein that the same kind of substitutions could be made on the β-form.

Screening Assays: Candidate agents may be screened for their ability to inhibit NKT cell activation. Assays to determine affinity and specificity of binding are known in the art, including competitive and non-competitive assays. Assays of interest include ELISA, RIA, flow cytometry, etc. Binding assays may bind CD1 to a solid matrix, then add the candidate ligand (agent) to the bound CD1. The affinity of binding can be measured by plasmon resonance spectroscopy (Biacore assay). Alternatively, the candidate blocking agent can be combined with the bound CD1 in the presence of a competitor, e.g. a glycolipid, etc.

Binding assays may also be performed to assess whether a candidate agent interferes with binding of molecules to CD1; or interferes with the interaction between NKT cell receptor and a CD1/glycolipid complex. An assay for determining whether a candidate agent can bind to the NKT cell receptor (NKTCR) may utilize a CD1 dimer or tetramer (see Kronenberg et al. (2001) P.N.A.S. 98:2950-2952). For example, a CD1 tetramer may be loaded with a candidate agent; and the resulting complex then contacted with NKTCR, usually NKT cells, and the level of binding quantitated, for example by flow cytometry. As a positive control, the binding of a CD1 tetramer/α-galactosyl ceramide may be quantitated; or used in a competitive binding assay. In some embodiments, the agent of interest will bind to the NKTCR under these conditions.

In other embodiments, an agent of interest will interfere with an agonist that binds to CD1 and TCR. Such blocking can be assayed by first loading the positive control (agonist such as α-galcer) onto CD1 dimers or tetramers, which tetramers may be detectably labeled. The resulting reagent is used to bind to a population of NKT cells, which binding is quantitated, e.g. by flow cytometry. To show that a candidate agent interrupts binding, the tetramer is pre-incubated with the candidate antagonist, then loaded with the agonist; and the resulting complex compared with the agonist complex for it's ability to bind to NKT cells. In some embodiments, the agent of interest will interfere with the interaction between binding of an agonist and CD1.

Generally a plurality of assay mixtures are run in parallel with different agent concentrations to obtain a differential response to the various concentrations. Typically, one of these concentrations serves as a negative control, i.e. at zero concentration or below the level of detection.

Assays of interest are directed to agents that inhibit the immune function of NKT cells. Assays of interest may be directed to binding assays for the NKT cell receptor, and/or CD1; or may utilize functional assays directed to an assessment of NKT cell activation, and/or animal models for NKT cell activation.

An in vitro functional assay that can be used for screening inhibitory compounds is based on the ability of a galactosyl ceramide to activate NKT cells in immune cell mixtures, such as mouse spleen cells, that include NKT cells and antigen presenting cells. Typically the α galactosyl ceramide is added to the cell culture for 24 hours, and activation is assayed by cell proliferation and the secretion of IL-4 and IFN-γ into the culture supernatant.

Screening for inhibitory compounds can be performed by pre-incubating the cell mixture with the candidate inhibitory molecule (antagonist), and then adding the α galactosyl ceramide activating molecule (agonist), and assaying cell proliferation. The supernatants are assayed 24 hours later for the secretion of cytokines Inhibitory potency is determined by the reduction in proliferation and cytokine secretion. Alternatively cell cultures could include purified NKT cells and purified antigen presenting cells, in particular, dendritic cells.

Candidate agents are obtained from a wide variety of sources including libraries of synthetic or natural compounds. For example, numerous means are available for random and directed synthesis of a wide variety of organic compounds and biomolecules. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

For the treatment of asthma, antibodies specific for CD1 are of interest to inhibit, or block NKT activation. Suitable antibodies may be obtained by immunizing a host animal with peptides comprising all or a portion of CD1 protein. Suitable host animals include mouse, rat sheep, goat, hamster, rabbit, etc. The origin of the protein immunogen may be mouse, human, rat, monkey etc. The host animal will generally be a different species than the immunogen, e.g. mouse CD1 used to immunize hamsters, human CD1 to immunize mice, etc. Peptides derived from such highly conserved regions may be used as immunogens to generate cross-specific antibodies. The immunogen may comprise the complete protein, or fragments and derivatives thereof. Preferred immunogens comprise all or a part of the extracellular domain of human CD1, where these residues may contain the post-translation modifications, such as glycosylation, found on the native CD1. Immunogens comprising the extracellular domain are produced in a variety of ways known in the art, e.g. expression of cloned genes using conventional recombinant methods, isolation from T cells, sorted cell populations expressing high levels of CD1, etc. Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using CD1 bound to an insoluble support, protein A sepharose, etc. For in vivo use, particularly for injection into humans, it is desirable to decrease the antigenicity of the blocking agent. An immune response of a recipient against the blocking agent will potentially decrease the period of time that the therapy is effective. There are several methods that may be pursued to provide human or humanized antibodies, including production of human antibodies in transgenic animal hosts, modification of animal antibodies to "humanize", or "resurface" the antibody; or selection of human antibody fragments in a phage display screening. A review of human and humanized antibodies may be found in Vaughan et al. (1998) Nat. Biotech. 16:535. Methods of humanizing antibodies are known in the art. The antibody of interest may be engineered by recombinant DNA techniques to substitute the CH1, CH2, CH3, hinge domains, and/or the framework domain with the corresponding human sequence (see WO 92/02190; Roguska et al. (1994) P.N.A.S. 91:969-973; Jones et al. (1986) Nature 321: 522-525; Padlan (1991) Mol. Immunol. 28:489-498).

A variety of other reagents may be included in the screening assay. These include reagents like salts, neutral proteins, e.g. albumin, detergents, etc which may be used to facilitate optimal protein-DNA binding and/or reduce non-specific or background interactions. Also reagents that otherwise improve the efficiency of the assay, such as protease inhibitors, nuclease inhibitors, anti-microbial agents, etc. may be used.

Functional assays of interest include an assessment of the functional activation of NKT cells in an in vitro or in vivo setting. Activation may be measured by proliferation of NKT cells; the release of cytokines, e.g. IFN-γ and/or IL-4; the killing of target cells; and the like. Positive controls for activation may include the use of α-galactosylceramide, presented by a CD1 expressing antigen presenting cells; or a cell-free analog thereof, e.g. a CD1 tetramer.

NKT cells may be isolated from patient peripheral blood using various affinity methods, e.g. flow cytometry, immunomagnetic beads, etc. Activation assays may be performed on NKT cell clones or NKT cell hybridomas, e.g. using human cells, rodent cells, etc. Assays for monitoring NKT cell activation are known in the art, and include proliferation assays and cytokine release assays, including ELISA spot assays.

Proliferation assays measure the level of NKT cell proliferation in response to a specific antigen. In an exemplary assay, mouse spleen cells, mixtures of purified NKT cells and dendritic cells, etc. are prepared and washed, then cultured in the presence of an activating agent, e.g. α-galactosylceramide. The cells are usually cultured for 24 hours to several days. Glycolipid-induced proliferation is assessed by the monitoring the synthesis of DNA by the cultures, e.g. incorporation of $^3$H-thymidine during the last 18 H of culture.

NKT cell cytotoxic assays measure the numbers of cytotoxic NKT cells having killing activity. NKT cells are tested for their ability to kill target cells. In an exemplary assay, target cells are labeled with $Na^{51}CrO_4$. The target cells are then added to a suspension of potentially activated NKT cells. The cytotoxicity is measured by quantitating the release of $Na^{51}CrO_4$ from lysed cells. Controls for spontaneous and total release are typically included in the assay. Percent specific $^{51}Cr$ release may be calculated based as a percentage of the spontaneous release.

Enzyme linked immunosorbent assay (ELISA) and other immunospecific assays may used to determine the cytokine profile of activated NKT cells, and may be used to monitor for the expression of such cytokines as IL-4, γ-IFN, etc. The capture antibodies may be any antibody specific for a cytokine of interest, where supernatants from the NKT cell cultures, as described above, are conveniently used as a source of antigen. After blocking and washing, labeled detector antibodies are added, and the concentrations of protein present determined as a function of the label that is bound.

II. Formulations

The NKT cell inhibitory agents are may be provided in solution or in any other pharmacologically suitable form for administration. The agents are formulated for administration in a manner customary for administration of such materials. Typical formulations are those provided in *Remington's Pharmaceutical Sciences*, latest edition, Mack Publishing Company, Easton, Pa. The route of administration will be selected based on the compound being administered, the status of the patient and disease that is being treated. A compound may be administered through different routes depending on the severity of the disease, e.g. emergency situations may require i.v. administration, acute but not life threatening situation may be treated orally, while chronic treatment can be administered by aerosol.

For therapeutic use, particularly in airway diseases, local delivery is preferred. Delivery by inhalation or insufflating aerosols provide high level concentrations of drug compared to the concentration absorbed systemically. Alternatively, the agent maybe administered by injection, including intramuscular, intravenous (IV), subcutaneous or peritoneal injection, most preferably IV and local injections. However, other modes of administration may also be used provided means are available to permit the agent to enter the systemic circulation, such as oral, transmucosal or transdermal formulations, which can be applied as suppositories, skin patches, or intranasally. Any suitable formulation that effects the transfer of the agent to the bloodstream or locally to the lungs may properly be used.

For injection, suitable formulations generally comprise aqueous solutions or suspensions using physiological saline, Hank's solution, or other buffers optionally including stabilizing agents or other minor components. Liposomal preparations and other forms of microemulsions can also be used. The agent may also be supplied in lyophilized form and reconstituted for administration. Transmucosal and transdermal administrations generally include agents that facilitate passage through the mucosal or dermal barrier, such as bile, salts, fusidic acid and its analogs, various detergents and the like. Oral administration is also possible (see, for example, Miyamoto et al. (2001) Nature 413(6855):531-4).

The nature of the formulation will depend to some extent on the nature of the agent chosen. A suitable formulation is prepared using known techniques and principles of formulation well known to those skilled in the art. The percentage of agent contained in a particular pharmaceutical composition will also depend on the nature of the formulation; the percentage may vary over a wide range from about 1% by weight to about 85% by weight.

Agents may be administered to the afflicted patient by means of a pharmaceutical delivery system for the inhalation route. The compounds may be formulated in a form suitable for administration by inhalation. The pharmaceutical delivery system is one that is suitable for respiratory therapy by topical administration of agents thereof to mucosal linings of the bronchi. This invention can utilize a system that depends on the power of a compressed gas to expel the agents from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed in this invention, the aerosol contains the therapeutically active compound, which can be dissolved, suspended, or emulsified in a mixture of a fluid carrier and a propellant. The aerosol can be in the form of a solution, suspension, emulsion, powder, or semi-solid preparation. Aerosols employed in the present invention are intended for administration as fine, solid particles or as liquid mists via the respiratory tract of a patient. Various types of propellants known to one of skill in the art can be utilized. Examples of suitable propellants include, but is not limited to, hydrocarbons or other suitable gas. In the case of the pressurized aerosol, the dosage unit may be determined by providing a value to deliver a metered amount.

The present invention can also be carried out with a nebulizer, which is an instrument that generates very fine liquid particles of substantially uniform size in a gas. Preferably, a liquid containing the agent is dispersed as droplets. The small droplets can be carried by a current of air through an outlet tube of the nebulizer. The resulting mist penetrates into the respiratory tract of the patient.

A powder composition containing the agent, with or without a lubricant, carrier, or propellant, can be administered to a mammal in need of therapy. This embodiment of the invention can be carried out with a conventional device for administering a powder pharmaceutical composition by inhalation. For example, a powder mixture of the compound and a suitable powder base such as lactose or starch may be presented in unit dosage form in for example capsular or cartridges, e.g. gelatin, or blister packs, from which the powder may be administered with the aid of an inhaler.

The microparticles containing the agent may be maintained as such, i.e. as a dry powder, in a container. During storage or in formulation, they may be mixed with any suitable pharmaceutical agents, carriers, bulking agents etc., and they may be processed by any technique desired to give a product having the properties intended for the ultimate therapeutic use. In particular, the formulation of particles for formulations that can be delivered to the lung, e.g. using a metered dose or dry powder inhaler, are known to those skilled in the art.

A "pharmaceutically acceptable excipient" may be used herein, and refers to a compound that is useful in preparing a pharmaceutical composition that is generally safe, non-toxic and neither biologically nor otherwise undesirable, and includes excipients that are acceptable for pharmaceutical use. A pharmaceutically acceptable excipient as used in the specification and claims includes both one and more than one such excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, phosphatidylcholine, cellulose, sterile water, syrup, and methyl cellulose.

The formulations can additionally include: lubricating agents such as talc, magnesium stearate, and mineral oil; wetting agents; emulsifying and suspending agents; and preserving agents such as methyl- and propylhydroxy-benzoates and benzyl alcohol.

The formulation containing the active agent of the present invention may be formulated with various excipients. Pharmaceutically acceptable excipients may be volatile or nonvolatile. Volatile excipients, when heated, are concurrently volatilized, aerosolized and inhaled with the antihistamine Classes of such excipients are known in the art and include, without limitation, gaseous, supercritical fluid, liquid and solid solvents. The following is a list of exemplary carriers within the classes: water; terpenes, such as menthol; alcohols, such as ethanol, propylene glycol, glycerol and other similar alcohols; dimethylformamide; dimethylacetamide; wax; supercritical carbon dioxide; dry ice; and mixtures thereof. Other examples of excipient include, by way of example only, surfactants are amphiphilic molecules having both a lipophilic and a hydrophilic moiety, with varying balance between these two characteristics. If the molecule is lipophilic, the low solubility of the substance in water may limit its usefulness. If the hydrophilic part overwhelmingly dominates, however, the surface active properties of the molecule may be minimal. To be effective, therefore, the surfactant must strike an appropriate balance between sufficient solubility and sufficient surface activity. All of the bile salts and bile salt derivatives (sodium salts of ursodeoxycholate, taurocholate, glycocholate, and taurodihydrofusidate) effectively enhance absorption in the lung.

Phospholipids, glycoside, octylglucopyranoside, alkyl glycosides, such as thioglucopyranosides and maltopyranosides, cyclodextrins and derivatives thereof effectively enhance nasal absorption, and may function similarly in the lung. Other potentially useful surfactants are sodium salicylate, sodium 5-methoxysalicylate, and the naturally occurring surfactants such as salts of glycyrrhizine acid, saponin glycosides and acyl carnitines.

Lipids may be used in the formulations of the present invention, such as, by way of example only, synthetic, semi-synthetic or naturally-occurring lipids, including phospholipids, tocopherols, sterols, fatty acids, glycoproteins such as albumin, negatively-charged lipids and cationic lipids. In terms of phosholipids, they could include such lipids as egg phosphatidylcholine (EPC), egg phosphatidylglycerol (EPG), egg phosphatidylinositol (EPI), egg phosphatidylserine (EPS), phosphatidylethanolamine (EPE), and phosphatidic acid (EPA); the soya counterparts, soy phosphatidylcholine (SPC); SPG, SPS, SPI, SPE, and SPA; the hydrogenated egg and soya counterparts (e.g., HEPC, HSPC), other phospholipids made up of ester linkages of fatty acids in the 2 and 3 of glycerol positions containing chains of 12 to 26 carbon atoms and different head groups in the I position of glycerol that include choline, glycerol, inositol, serine, ethanolamine, as well as the corresponding phosphatidic acids. The chains on these fatty acids can be saturated or unsaturated, and the phospholipid may be made up of fatty acids of different chain lengths and different degrees of unsaturation. In particular, the compositions of the formulations can include DPPC, a major constituent of naturally-occurring lung surfactant. Other examples include dimyristoylphosphatidylcholine (DMPC) and dimyristoylphosphatidylglycerol (DMPG) dipalmitoylphosphatidylcholine (DPPC) and dipalmitoylphosphatidylglycerol (DPPG) distearoylphosphatidylcholine (DSPC) and distearoylphosphatidylglycerol (DSPG), dioleylphosphatidyl-ethanolamine (DOPE) and mixed phospholipids like palmitoylstearoylphosphatidylcholine (PSPC) and palmitoylstearolphosphatidylglycerol (PSPG), and single acylated phospholipids like monooleoylphosphatidylethanolamine (MOPE). The sterols can include, cholesterol, esters of cholesterol including cholesterol hemisuccinate, salts of cholesterol including cholesterol hydrogen sulfate and cholesterol sulfate, ergosterol, esters of ergosterol including ergosterol hemi-succinate, salts of ergosterol including ergosterol hydrogen sulfate and ergosterol sulfate, lanosterol, esters of lanosterol including lanosterol hemi-succinate, salts of lanosterol including lanosterol hydrogen sulfate and lanosterol sulfate. The tocopherols can include tocopherols, esters of tocopherols including tocopherol hemi-succinates, salts of tocopherols including tocopherol hydrogen sulfates and tocopherol sulfates. The term "sterol compound" includes sterols, tocopherols and the like.

The cationic lipids used can include ammonium salts of fatty acids, phospholids and glycerides. The fatty acids include fatty acids of carbon chain lengths of 12 to 26 carbon atoms that are either saturated or unsaturated. Some specific examples include: myristylamine, palmitylamine, laurylamine and stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9-(Z)-octadecenyloxy)-prop-1-yl-N,N,N-trimethylammonium chloride (DOTMA) and 1,2-bis(oleoyloxy)-3-(trimethylammonio) propane (DOTAP). The negatively-charged lipids which can be used include phosphatidyl-glycerols (PGs), phosphatidic acids (PAs), phosphatidylinositols (Pls) and the phosphatidyl serines (PSs). Examples include DMPG, DPPG, DSPG, DMPA, DPPA, DSPA, DMPI, DPPI, DSPI, DMPS, DPPS and DSPS.

For ionic enhancers (e.g., the anionic surfactants described above), the nature of the counterion may be important. The particular counterion selected may influence the powder properties, solubility, stability, hygroscopicity, and local/systemic toxicity of the enhancer or of any formulation containing the enhancer. It may also affect the stability and/or solubility of the active agent with which it is combined. In general, monovalent metallic ions such as sodium, potassium, lithium, rubidium, and cesium, ammonia and organic amines.

Examples of such organic amines include ethanolamine, diethanolamine, triethanolamine, 2-amino-2-methylethylamine, betaines, ethylenediamine, N,N-dibensylethylenetetraamine, arginine, hexamethylenetetraamine, histidine, N-methylpiperidine, lysine, piperazine, spermidine, spermine and tris(hydroxymethyl)aminomethane.

Other excipients that may be useful in the formulations of the NKT cell inhibitory agent can be, by way of example only, starch microspheres, and chelators such as, a sodium salt of ethylenediaminetetraacetic acid (EDTA).

The preferred ratio for NKT cell inhibitory agent/excipient (or NKT cell inhibitory agent/excipient/diluent) combination can be readily determined by one of ordinary skill in the art of pharmacology by standard methods, based on such criteria as efficient, consistent delivery of the optimal dosage, minimization of side effects, and acceptable rate of absorption.

There are several different types of inhalation methodologies which can be employed in connection with the present invention. Antagonists of the present invention can be formulated in basically three different types of formulations for inhalation. First, inhibitors of the invention can be formulated with low boiling point propellants. Such formulations are generally administered by conventional meter dose inhalers (MDI's). However, conventional MDI's can be modified so as to increase the ability to obtain repeatable dosing by utilizing technology which measures the inspiratory volume and flow rate of the patient as discussed within U.S. Pat. Nos. 5,404,871 and 5,542,410. Alternatively, the inhibitors of the present invention can be formulated in aqueous or ethanolic solutions and delivered by conventional nebulizers. However, more preferably, such solution formulations are aerosolized using devices and systems such as disclosed within U.S. Pat. Nos. 5,497,763; 5,544,646; 5,718,222; and 5,660,166. Lastly, inhibitor compounds of the present invention can be formulated into dry powder formulations. Such formulations can be administered by simply inhaling the dry powder formulation after creating an aerosol mist of the powder. Technology for carrying such out is described within U.S. Pat. No. 5,775,320 issued Jul. 7, 1998 and U.S. Pat. No. 5,740,794 issued Apr. 21, 1998.

For oral preparations, the agents are used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and in some embodiments, with diluents, buffering agents, moistening agents, preservatives and flavoring agents.

In one embodiment of the invention, the oral formulations comprise enteric coatings, so that the active agent is delivered to the intestinal tract. Enteric formulations are often used to protect an active ingredient from the strongly acid contents of the stomach. Such formulations are created by coating a solid dosage form with a film of a polymer that is insoluble in acid environments and soluble in basic environments. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate.

Other enteric formulations comprise engineered polymer microspheres made of biologically erodable polymers, which display strong adhesive interactions with gastrointestinal mucus and cellular linings, can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) J Control Release 71(3):307-18.

Formulations are typically provided in a unit dosage form, where the term "unit dosage form," refers to physically discrete units suitable as unitary dosages for human subjects, each unit containing a predetermined quantity calculated in an amount sufficient to produce the desired effect in association with a pharmaceutically acceptable diluent, carrier or vehicle. The specifications for the unit dosage forms of the present invention depend on the particular agent employed and the effect to be achieved, and the pharmacodynamics associated with each complex in the host.

III. Co-formulations

The subject NK T cell inhibitory agent may be formulated or administered in conjunction with other agents that act to relieve the symptoms of SLE, asthma, etc. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. The side effects of these drugs include anemia, low white blood cell count, and increased risk of infection. Other agents, e.g. methotrexate and cyclosporin are used to control the symptoms of lupus. Both are immunomodulating drugs which have their own side effects. Anticoagulants are employed to prevent blood from clotting rapidly. They range from aspirin at very low dose which prevents platelets from sticking, to heparin/coumadin.

Medicaments which may be administered in conjunction with NK T cell inhibitory agent according to the invention include any drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament.

The NKT cell inhibitory agents are administered to a patient suffering from undesirable activation of NKT cells, which patients may include individuals suffering from allergic diseases, including asthma, from SLE, and the like. SLE patients may suffer from skin, joint, kidney, and/or central nervous system indicia of the disease. In other embodiments, cancer patients may benefit from methods to inhibit NKT cells, in order to relieve the down-regulation of immunosurveillance. Atherosclerosis patients may also benefit from the methods of the invention.

IV. Dosages

Various methods for administration may be employed. The agent formulation may be inhaled, injected intravascularly, subcutaneously, peritoneally, etc. The dosage of the therapeutic formulation will vary widely, depending upon the nature of the disease, the frequency of administration, the manner of administration, the purpose of the administration, the clearance of the agent from the host, and the like. The dosage administered will vary depending on known factors, such as the pharmacodynamic characteristics of the particular agent, mode and route of administration, age, health and weight of the recipient, nature and extent of symptoms, concurrent treatments, frequency of treatment and effect desired. The dose may be administered as infrequently as weekly or biweekly, or fractionated into smaller doses and administered daily, semi-weekly, etc. to maintain an effective dosage level. Generally, a daily dosage of active ingredient can be about 0.1 to 100 mg/kg of body weight. Dosage forms suitable for internal administration generally contain from about 0.1 mg to 500 mgs of active ingredient per unit. The active ingredient may vary from 0.5 to 95% by weight based on the total weight of the composition.

The active ingredient may vary from 0.5 to 95% by weight based on the total weight of the composition.

In some embodiments, dosage of active ingredient can be less than 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% by weight based on the total weight of the composition.

In some embodiments, dosage of active ingredient is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% by weight based on the total weight of the composition.

In some embodiments, dosage of active ingredient is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g per kg of body weight.

In some embodiments, dosage of active ingredient is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g 0.15 g, 0.2 g 0.25 g, 0.3 g 0.35 g, 0.4 g 0.45 g, 0.5 g, 0.55 g, 0.6 g 0.65 g, 0.7 g, 0.75 g, 0.8 g 0.85 g, 0.9 g, 0.95 g, 1 g, 1.5 g, 2 g, 2.5 g, 3 g, 3.5, 4 g, 4.5 g, 5 g, 5.5 g, 6 g, 6.5 g, 7 g, 7.5 g, 8 g, 8.5 g, 9 g, 9.5 g, or 10 g per kg of body weight.

In some embodiments, a dosage of active ingredient is 0.0001-10 g, 0.0005-9 g, 0.001-8 g, 0.005-7 g, 0.01-6 g, 0.05-5 g, 0.1-4 g, 0.5-4 g, or 1-3 g per kg of body weight.

Generally, a daily dosage of active ingredient can be about 0.1 to 100 mg/kg of body weight. Dosage forms suitable for internal administration generally contain from about 0.1 mg to 500 mgs of active ingredient per unit. In some embodiments of the present invention dosage of the active ingredient can be 0.1-10 mg/kg of body weight. In some embodiments of the present invention dosage of the active ingredient can be 0.1-5 mg/kg of body weight. In some embodiments of the present invention dosage of the active ingredient can be 0.1-2 mg/kg of body weight. In some embodiments of the present invention dosage of the active ingredient can be 0.5-10 mg/kg of body weight. In some embodiments of the present invention dosage of the active ingredient can be 0.5-2 mg/kg of body weight.

In some aspects of the present invention, unit dose formulations are provided for administration of NKT cell inhibiotry agent formulation to a patient. Such unit dose can have, for example, a total volume of less than 50 mL, 40 mL, 30 mL, 20 mL, 10 mL, 9 mL, 8 mL, 7 mL, 6 mL, 5 mL, 4 mL, 3 mL, 2 mL, 1 mL, 0.9 mL, 0.8 mL, 0.7 mL, 0.6 mL, 0.5 mL, 0.4 mL, 0.3 mL, 0.2 mL, 0.1 mL, 0.09 mL, 0.08 mL, 0.07 mL, 0.06 mL, 0.05 mL, 0.04 mL, 0.03 mL, 0.02 mL, 0.01 mL, 0.009 mL, 0.008 mL, 0.007 mL, 0.006 mL, 0.005 mL, 0.004 mL, 0.003 mL, 0.002 mL, 0.001 mL, 0.0009 mL, 0.0008 mL, 0.0007 mL, 0.0006 mL, 0.0005 mL, 0.0004 mL, 0.0003 mL, 0.0002 mL, or 0.0001 mL. In some embodiments, such unit dose may have a total volume of more than 0.2 mL and less than 500 mL. In some embodiments, such unit dose may have a total volume of less than 0.1 mL. In some embodiments, such unit dose may have a total volume of less than 0.1 mL. In some embodiments, such unit dose may have total volume of 0.1-0.2 mL (inclusive of 0.1 mL and 0.2 mL). In some embodiments, such unit dose may have a total volume of less than 0.1 and greater than 0.2.

In some embodiments, a unit dose has a total volume in the range of 0.0001-500 mL, 0.0005-400 mL, 0.001-300 mL, 0.005-200 mL, 0.01-100 mL, 0.05-90 mL, 0.06-80 mL, 0.07-70 mL, 0.08-60 mL, 0.09-50 mL, 0.1-40 mL, 0.2-30 mL, 0.3-29 mL, 0.4-28 mL, 0.5-27 mL, 0.6-26 mL, 0.7-25 mL, 0.8-24 mL, 0.9-23 mL, 10-22 mL, 11-21 mL, 12-20 mL, 13-19 mL, 14-18 mL, or 15-17 mL per target site.

V. Devices

In order to deliver the relatively small volumes of the formulations of the present invention for inhalation in the relatively short dosing periods, the formulations can be administered with the use of an inhalation device having a relatively high rate of aerosol output. Useful devices may also exhibit high emitted dose efficiency (i.e., low residual volume in the device). In order to increase the overall efficiency of the system, emission may additionally be limited to periods of actual inhalation by the patient (i.e., breath actuated). Thus, conventional air jet nebulizers may exhibit a rate of aerosol output on the order of 3 µl/sec, of about 4 μl/sec, of about 5 μl/sec or not less than about 8 μl/sec. The inhalation devices useful for practice in the present invention may release at least about 55%, at least about 65%, at least about 75%, more preferably at least about 80% and most preferably at least about 85% of the loaded dose as aerosol for inhalation by the patient. In some embodiments, inhalation devices for use in the present invention may be breath actuated, and restricted to delivery of aerosolized particles of the formulation containing NK T cell inhibitory agent to the period of actual inhalation by the patient. The inhaler can be a hand-held, self-contained, and easily transported inhaler. In other embodiments of the invention, devices useful for delivering the concentrated NK T cell inhibitory agent formulations of the invention include conventional air-jet nebulizers coupled with a compressor capable of higher than conventional output pressures.

The following examples are offered by way of illustration and not by way of limitation.

EXPERIMENTAL

Example 1

The i.p. injection of a galactosyl ceramide (obtained from Brigham Young University, Provo, Utah) into C57BL/6 mice increases serum levels of IL-4 and IFN-γ by selectively activating NKT cells. Injection of C12 β galactosyl ceramide (Avanti Lipids, Inc.) i.p. antagonizes the ability of α galactosyl ceramide to raise the levels of IL-4, interferon-gamma, and IgE in the serum of these mice.

Male C57BL/6 mice of about 8 weeks of age were given either 100 μg of β galactosyl ceramide (β Galcer) i.p., 0.1 μg of α galactosyl ceramide (α Galcer) i.p., 100 μg β Galcer i.p. either 1 hour before or at the same time as 0.1 μg α Galcer i.p., or no treatment. β-Galcer was obtained from Avanti Lipids Inc. Glycolipids were in aqueous solutions with PBS. Cytokine levels were determined by ELISA as previously described by Zeng et al. (2003), supra. All mice were sacrificed 6 hours later, and serum levels of IFN-γ and IL-4 were determined, as shown in FIGS. 1A and 1B.

The assay for IFN-γ showed that normal (untreated) mice had a level of about 50 pg/ml. The injection of β Galcer above did not increase the level, but the injection of α Galcer alone increased the level more than two fold. However, when β Galcer was given 1 hour before α Galcer or at the same time as α Galcer then the levels were below 40 pg/ml. The results show that β Galcer blocked the increase that was induced by α Galcer.

A similar pattern was observed when serum IL-4 levels were determined Untreated mice had about 100 pg/ml IL-4, and 100 μg β Galcer alone did not increase the level. However, 0.1 μg α Galcer increased the level by about 10 fold to 1000 pg/ml. When 100 μg β Galcer was given one hour before 0.1 μg α Galcer then the increase was completely blocked, and when both glycolipids were given at the same time, the IL-4 level was about 250 pg/ml. The results show that β Galcer can inhibit not only the increase in the level of serum IFN-γ, induced by α Galcer, but can also inhibit the increase in the level of IL-4. We conclude that β Galcer can block the activation of NKT cells in vivo induced by α Galcer as judged by secretion of cytokines into the serum.

In a separate experiment, mean serum IgE levels of groups of three C57BL/6 mice were measured before or 10 days after a single i.p. injection of 0.1 μg α Galcer alone, 100 μg β Galcer alone, or 100 μg of β Galcer injected 1 hour before 0.1 μg α Galcer. The results, shown in FIGS. 1C and 1D, demonstrate that α Galcer alone raised the IgE level about three fold to about 500 ng/ml, β Galcer induced a smaller increase to about 400 μg/ml, and the combination of glycolipids induced a level of about 250 μg/ml. The bars show means of triplicate determinations, and the brackets show standard deviations. The only significant difference between before and after serum levels was observed with α Galcer alone ($p<0.05$) as judged by the student-t-test of independent means. We conclude that β Galcer blocks the increase in serum IgE levels induced by α Galcer. No significant change is seen with the control IgG2c expression.

Example 2

Effects of β-GalCer on Asthma

In murine model of asthma, β-GalCer was administered to OVA-immunized BALB/c mice, or mice with α-GalCer induced airway hyperresponsiveness (AHR).

Materials and Methods

Animals: BALB/cByJ mice were obtained from the Jackson Laboratory, Bar Harbor, Me. The Stanford University Committee on Animal Welfare approved animal protocols used in this study.

Monoclonal Antibodies: Monoclonal antibodies were purified from ascites by ammonium sulfate precipitation and ion-exchange chromatography. The following hybridomas were used: R46A2 (anti-IFN-y mAb) obtained from ATCC (American Type Culture Collection, Rockville, Md.); XMG1.2 (anti-IFN-y antibody); BVD4-1D11, BVD6-24G2 (anti-IL-4 mAb). Anti-38C13 idiotype mAb 4G10 (rat IgG2a) was used as isotype control.

Immunizations. BALB/c mice were primed in the footpads with OVA (100 μg/mouse) adsorbed to 200 μg of alum (Al $[OH]_3$). Mice were challenged with 50 μg OVA in 50 μl NaCl 0.9% intranasally 7, 8, and 9 days later. One day after the last intranasal challenge with OVA, airway hyperreactivity was measured from conscious mice after inhalation of increasing concentrations of methacholine in a whole body plethysmograph Immunization with α-GalCer was performed as described.

To facilitate pulmonary aspiration during intranasal administration of antigen, mice were lightly anesthetized intraperitoneally (i.p.) with 0.25 ml of ketamine (0.44 mg/ml)/xylazine (6.3 mg/ml) in normal saline. 75% of the intranasally administered antigen can be subsequently detected in the lungs (Tsuyuki et al. (1997) J. Exp. Med. 185:1671-9.

Cytokine ELISA. ELISAS were performed as previously described Macaulay et al. (1998) J. Immunol. 160:1694-1700. The antibody pairs used were as follows, listed by capture/biotinylated detection: IL-4, BVD4-1D11/BVD6-24G2; IFN-γ, R4-6A2/XMG1.2. Recombinant cytokine were used as standards, with curves generated in 1:2 dilutions from 500 to 39 pg/ml for IL-4, and 20-2, 156 ng/ml for IFN-γ.

Measurement of anti-OVA antibody isotypes. Mice were bled at the time of sacrifice and OVA-specific antibody was measured using a modified antigen-specific ELISA. For measurement of OVA specific IgG, plates were coated overnight with 5 μg/ml OVA. After washing and blocking, serial diluted sera were added to the plates. Following overnight incubation, the plates were developed using HRPO-conjugated goat anti-IgG subclass-specific antibodies (Southern Biotechnology Associates, Birmingham, Ala.). After additional washing, OPD substrate was added, the plates developed and the OD determined at 492 nm Anti-OVA IgG1 mAb 6C1 and anti-OVA IgG2a mAb 3A11 were used as standards for quantitation of each IgG subclass. Determination of OVA-specific IgE was performed by ELISA, using rat anti-mouse IgE mAb EM95 (5.0 µg/ml) to coat plates. After the samples were applied and incubated overnight, plates were washed and biotinylated OVA (10 µg/ml) was added. Two hours later, plates were washed and HRPO-conjugated streptavidin (Southern Biotechnology Associates) was added. Plates were developed with OPD substrate and the OD determined at 492 nm Sera from mice hyperimmunized with OVA in alum was quantitated for IgE and used as standard for the OVA-specific IgE ELISA.

Measurement of Airway Responsiveness. Airway responsiveness was assessed by methacholine-induced airflow obstruction from conscious mice placed in a whole body plethysmograph (model PLY 3211, Buxco Electronics Inc., Troy, N.Y.). Pulmonary airflow obstruction was measured by Penh using the following formula:

$$Penh = \left(\frac{Te}{RT} - 1\right) \times \left(\frac{PEF}{PIF}\right),$$

where Penh=enhanced pause (dimensionless), Te=expiratory time, RT=relaxation time, PEF=peak expiratory flow (ml/s), and PIF=peak inspiratory flow (ml/s) (Hamelmann et al. (1997) Am. J. Respir. Crit. Care Med. 156:766-75. Enhanced pause (Penh), minute volume, tidal volume, and breathing frequency were obtained from chamber, pressure, measured with a transducer (model TRD5100) connected to preamplifier modules (model MAX2270) and analyzed by system XA software (model SFT 1810). Measurements of methacholine responsiveness were obtained by exposing mice for 2 min to NaCl 0.9%

Collection of BAL Fluid and Lung Histology. Animals were injected i.p. with a lethal dose of phenobarbital (450 mg/kg). The trachea was cannulated, and the lung was then lavaged with 0.8 ml of PBS three times, and the fluid pooled. Cells in the lavage fluid were counted using a hemocytometer and BAL cell differentials were determined on slide preparations stained with Hansel Stain (Lide Laboratories, Florissant, Mo.). At least 200 cells were differentiated by light microscopy based on conventional morphologic criteria. In some animals, no BAL was performed but lungs were removed, washed with PBS, fixed in 10% formalin and stained with hematoxylin and eosin.

Results.

Figure 2A:
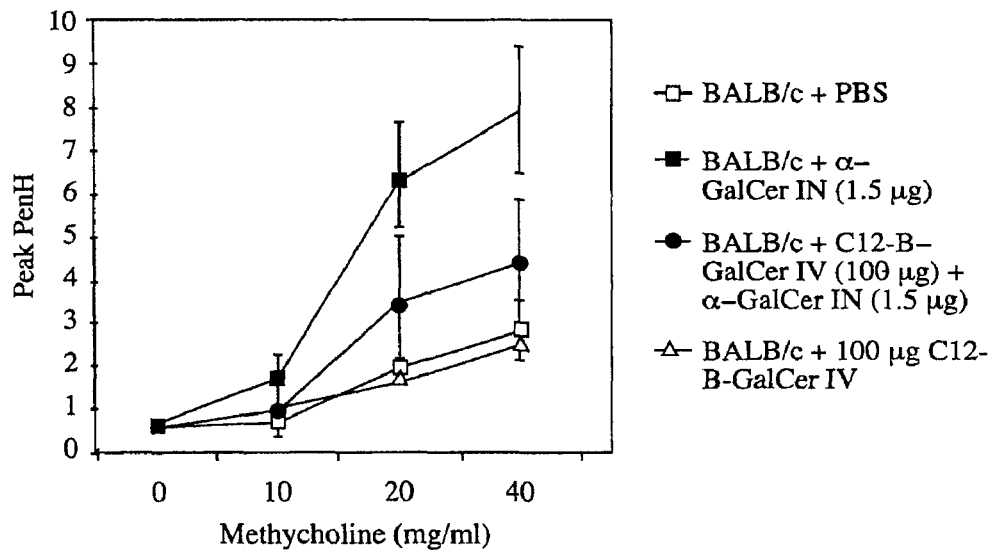
FIG. 2A-2B. Treatment with C12-$\beta$-GalCer blocks $\alpha$-GalCer induced AHR.
Figure 2B:
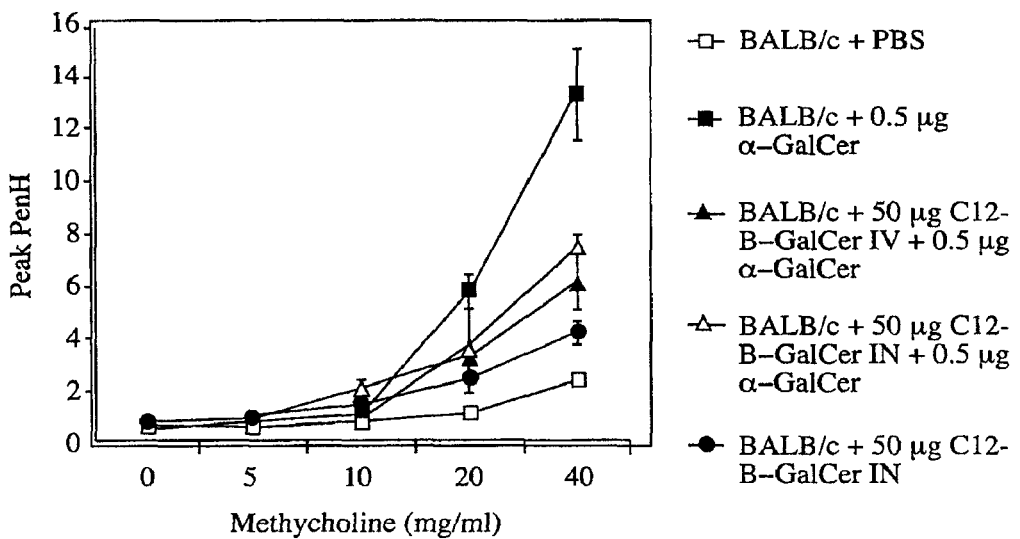

Treatment with C12-β-GalCer blocks α-GalCer induced AHR. As shown in FIG. 2, i.v. administration of 100 µg C12-β-GalCer administered 2 hours prior to 1.5 µg α-GalCer i.n. administration greatly reduces AHR at 24 hours. i.v. administration of C12-β-GalCer alone does not induce any AHR by itself (b) i.n. and i.v. administration of 50 µg C12-α-GalCer 2 hours prior to i.n. administration of 0.5 µg α-Gal-Cer greatly reduces 24 hours AHR, although C12-β-GalCer administered i.n. induces mild AHR. A minimum of 4 mice per group were used.

Figure 3A:
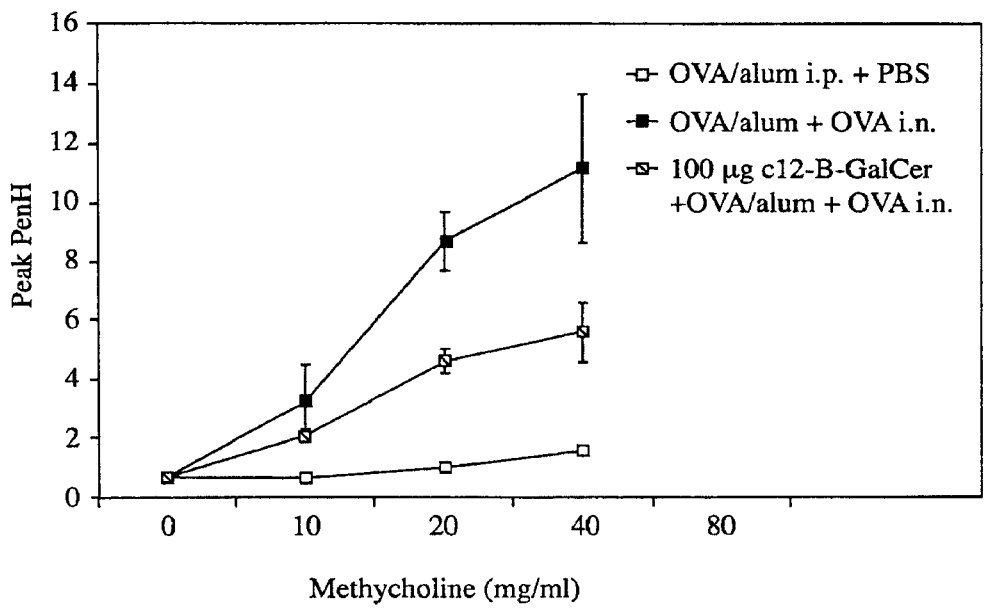
FIG. 3A-3C. Treatment with C12-$\beta$-GalCer reduces OVA/alum induced AHR.
Figure 3B:
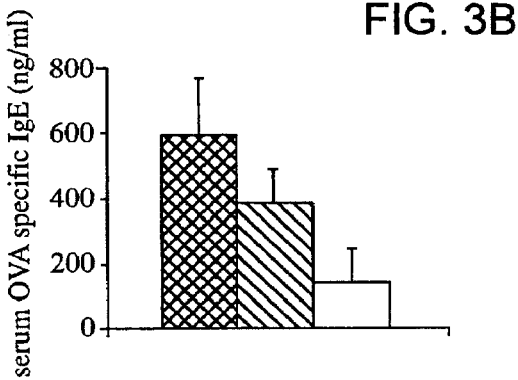
Figure 3C:
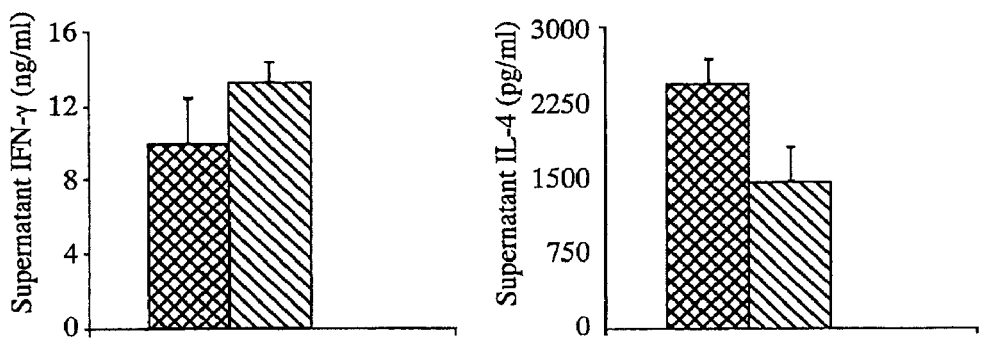

Treatment with C12-β-GalCer reduces OVA/alum induced AHR. As shown in FIG. 3, mice were sensitized by i.p. injection of 100 µg OVA with 200 µl aluminum hydroxide (alum) and then challenged i.n. with 50 µg OVA 7.8 and 9 days later. (a) AHR was measured on day 10. C12-β-GalCer was administered i.v. (100 µg) 1 day prior to OVA/alum sensitization and 6 hours prior to each i.n. challenge (100 µg). The treatment was shown to reduce AHR. (b) Serum OVA-specific IgE was reduced in C12-β-GalCer treated group. (c) Lymph node cells from C12-β-GalCer treated group produced slightly more IFN-γ and less IL-4 after four days in culture with 62.5 µg/ml OVA (5.0*10⁶ cells per well). Four mice were tested per group.

Figure 4A:
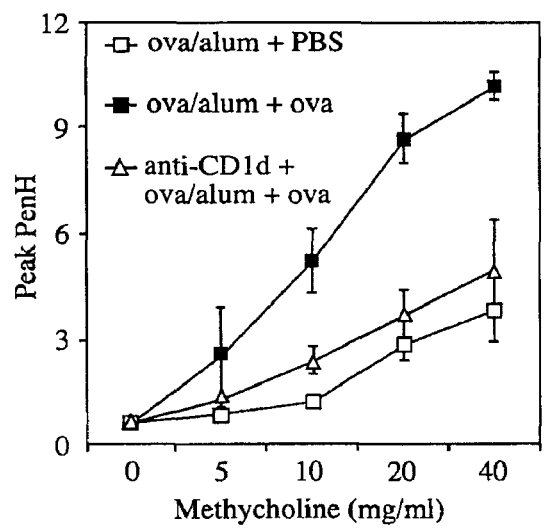
FIG. 4A-4B. Treatment with anti-CD1d antibody (HB323) blocks OVA/alum induced airway hyperresponsiveness (AHR).
Figure 4B:
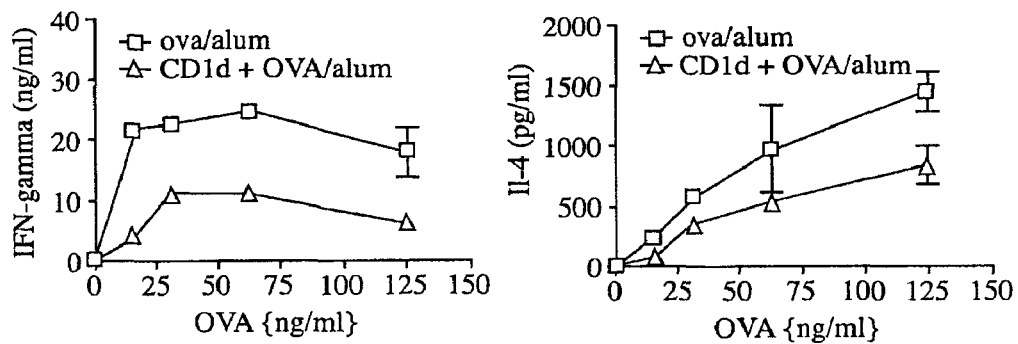

Treatment with anti-CD1d antibody (H8323) blocks OVA/alum induced AHR. As shown in FIG. 4, (a) Mice were sensitized by i.p. injection of 100 µg OVA with 200 µl aluminum hydroxide (alum) and then challenged i.n. with 50 µg OVA 7.8 and 9 days later. AHR was measured on day 10. Anti-CD1d antibody was administered i.p. 1 day prior to OVA/alum sensitization (500 µg) and again just prior to i.n. challenge (500 µg). The treatment was shown to reduce AHR. (b) Treatment with anti-CD1d antibody (HB323) reduces lymph node cytokine production. Lymph node cultures of 5.0×10⁵ cells per well were established on day 11 after OVA/alum sensitization and airway challenge. Cultures were treated with OVA titrated from 125 µg/ml and supernatant cytokine was determined by ELISA. A minimum of 4 mice per group were used, data is representative of 2 experiments.

C12-β-GalCer causes more serum IFN-γ to be produced following α-GalCer induced AHR. Histology demonstrates reduced peri-bronchiolar eosinophilic inflammation with C12-β-GalCer treatment. Importantly, i.v. injection of C12-β-GalCer by itself does not result in any lung inflammation. The C12-β-GalCer treated group had large bronchial and mediastinal lymph nodes. These mice showed reduced but present eosinophilic infiltration of the lungs by histology with possibly more neutrophilia than OVA/alum positive control. The histology also demonstrates that eosinophilic inflammation is reduced (but still present) in the lungs of anti-CD1d treated mice. While HB323 blockade provides the best results, the use of the 1B1 anti-CD1d antibody also causes a reduction in AHR.

These data demonstrate the involvement of NKT cells in the development of AHR and asthma, and further demonstrate the effectiveness of the blocking agent □-GalCer, and anti-CD1, in the treatment of this disease.

Example 3

Oral Administration of Inhibitory Agents

Doses of β-galactosyl ceramide ranging from 100-800 µg/mouse were administered orally. Cytokine levels of IFN-γ and IL-4 were determined by ELISA as previously described by Zeng et al. (2003), supra. from serum levels.

Figure 5:
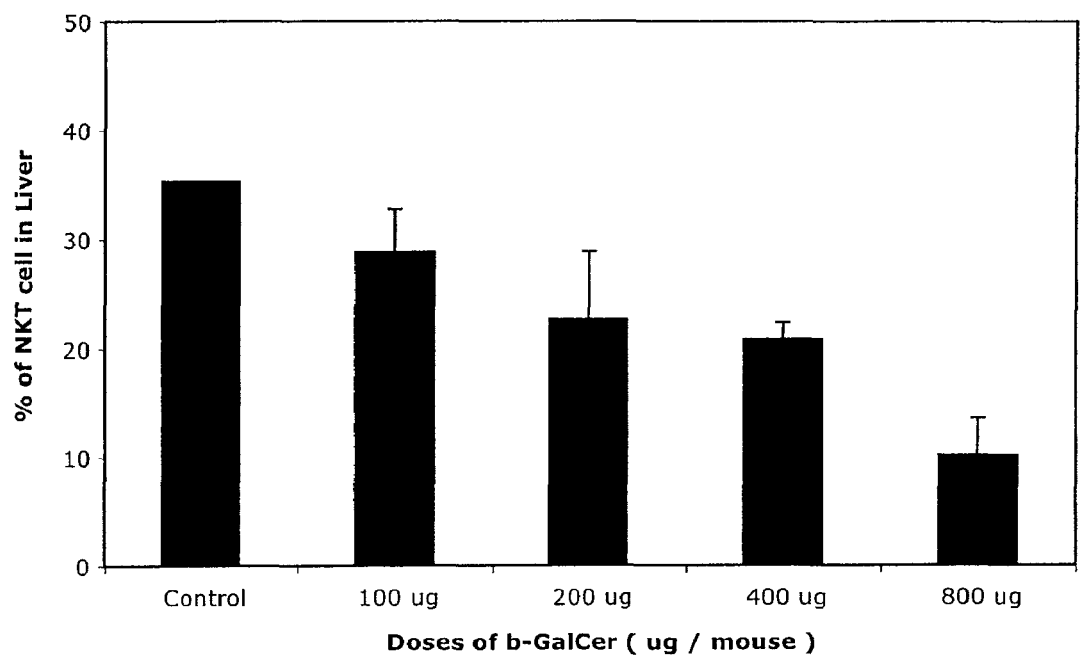
FIG. 5. Oral administration of $\beta$-galactosyl ceramide.

The assay for IFN-γ showed that at 24 hours after administration, there was no increase in serum levels at any dose. A similar pattern was observed when serum IL-4 levels were determined As shown in FIG. 5, the oral administration of β-galactosyl ceramide resulted in decreased staining for NKT cell markers in the liver.

The dosages of 100-800 µg/mouse are equivalent to a dose of 4-32 mg/kg. Using the FDA guidelines for human equivalence, the human equivalent dose is 0.32-2.6 mg/kg.

Example 4

Treatment of Lupus

In a murine model for systemic lupus erythematosus, the NZBxNZW mouse, animals were injected twice weekly with one of: PBS, 50 μg/mouse β-galactosyl ceramide, or 100 μg/mouse β-galactosyl ceramide. The animals were analyzed for proteinuria, which is an indication of the development of lupus. In the control group of 15 mice, at 38 weeks, approximately 30% of the mice were without proteinuria, while approximately 80% of the mice treated with the high dose of β-galactosyl ceramide were without proteinuria. These data indicate that β-galactosyl ceramide can inhibit the progression of lupus in this model.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for relieving asthma-associated airway hyperresponsiveness (AHR) in a patient, comprising: administering to the patient an effective dose of an anti-CD1d antibody, wherein the anti-CD1d antibody relieves asthma-associated AHR in the patient.

2. A method according to claim 1, further comprising detecting activated NKT cells in a sample obtained from the patient.

3. A method according to claim 2, further comprising detecting the presence of one or more of (i) eosinophils, (ii) mast cells, (iii) basophils, (iv) $CD25^+$ T lymphocytes, (v) $CD4^+$ T lymphocytes or (vi) neutrophils in the sample.

4. A method according to claim 2, wherein the activated NKT cells are detected by a proliferation assay, cytokine release assay or NKT cell cytotoxic assay.

5. A method according to claim 2, wherein the activated NKT cells are detected by measuring IFN-γ and/or IL-4 secretion of activated NKT cells.

6. A method according to claim 2, wherein the sample is obtained from the lung or serum.

7. A method according to claim 6, wherein the lung sample is a sputum or BAL sample.

8. A method according to claim 1, wherein the anti-CD1d antibody is administered locally or systemically.

9. A method according to claim 8, wherein local administration comprises inhalation or insufflation.

10. A method according to claim 8, wherein systemic administration comprises intramuscular, intravenous, subcutaneous, peritoneal, local injection, oral, transmucosal, transdermal, or intranasal administration.

11. A method according to claim 1, further comprising measuring pulmonary airflow obstruction in the patient, wherein a change in flow relative to a patient to which an anti-CD1d antibody has not been administered is determinative of impaired lung function.

12. A method according to claim 1, wherein the patient is a human being.

* * * * *